United States Patent [19]

Hauel et al.

[11] Patent Number: 5,459,147

[45] Date of Patent: Oct. 17, 1995

[54] SUBSTITUTED BENZIMIDAZOLYL DERIVATIVES AND PHARMACEUTICAL COMPOSITIONS CONTAINING THESE COMPOUNDS

[75] Inventors: Norbert Hauel, Schemmerhofen; Uwe Ries; Berthold Narr, both of Biberach; Jacques van Meel, Mittelbiberach; Wolfgang Wienen, Äpfingen; Michael Entzeroth, Warthausen, all of Germany

[73] Assignee: Dr. Karl Thomae GmbH, Biberach an der Riss, Germany

[21] Appl. No.: 237,710

[22] Filed: May 3, 1994

Related U.S. Application Data

[63] Continuation of Ser. No. 25,303, Mar. 2, 1993, abandoned.

[30] Foreign Application Priority Data

Mar. 12, 1992 [DE] Germany .................. 42 07 904.7

[51] Int. Cl.$^6$ .............. A61K 31/435; A61K 31/415; C07D 235/20; C07D 71/04
[52] U.S. Cl. .............. 514/303; 514/234.5; 514/249; 514/300; 514/368; 514/394; 514/395; 514/248; 514/258; 514/266; 544/139; 544/236; 544/277; 544/281; 544/350; 546/118; 546/121; 546/199; 548/154; 548/252; 548/253; 548/254; 548/305.7
[58] Field of Search .................. 544/139, 236, 544/277, 350, 281; 546/121, 118, 199; 548/154, 252, 253, 254, 305.7; 514/234.5, 249, 300, 303, 368, 394, 395, 248, 249, 258, 266

[56] References Cited

U.S. PATENT DOCUMENTS 5,190,942  3/1993  Poss ..................... 548/305.7

FOREIGN PATENT DOCUMENTS 0468470  1/1992  Germany .
0502314  9/1992  Germany .

*Primary Examiner*—Bernard Dentz
*Attorney, Agent, or Firm*—Robert P. Raymond; Alan R. Stempel; Mary-Ellen M. Devlin

[57] ABSTRACT

The invention relates to substituted benzimidazolyl derivatives of the general formula wherein A and $R_a$ to $R_c$ are defined as in claim 1, the mixtures of position isomers thereof and the salts thereof which have valuable properties.

These compounds have valuable pharmacological properties, particularly angiotensin-antagonistic effects and preferably angiotensin-II-antagonistic effects.

12 Claims, No Drawings

SUBSTITUTED BENZIMIDAZOLYL DERIVATIVES AND PHARMACEUTICAL COMPOSITIONS CONTAINING THESE COMPOUNDS

This is a continuation of application Ser. No. 08/025,303, filed Mar. 2, 1993, now abandoned.

The present invention relates to new substituted benzimidazolyl derivatives of general formula

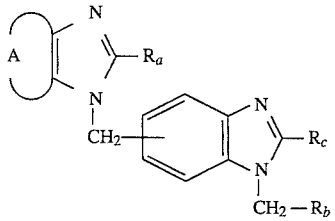

the mixtures of position isomers thereof and the salts thereof, more particularly for pharmaceutical use the physiologically acceptable salts thereof with inorganic or organic acids or bases, which have valuable pharmacological properties, particularly angiotensin-antagonistic effects, preferably angiotensin-II-antagonistic effects.

In the above general formula

A denotes a 1,4-butadienylene group substituted by the groups $R_1$ and $R_2$ and wherein additionally an unsubstituted methine group may be replaced by a nitrogen atom, wherein $R_1$ denotes a hydrogen, fluorine, chlorine or bromine atom, a trifluoromethyl group or a $C_{1-3}$-alkyl group and $R_2$ denotes a hydrogen atom, a $C_{1-3}$-alkyl group, a carboxy group, an alkoxycarbonyl group having a total of 2 to 6 carbon atoms, a $C_{2-5}$-alkoxy group which is substituted in the 2-, 3-, 4- or 5-position by an imidazolyl, benzimidazolyl or tetrahydrobenzimidazolyl group, an alkanoylamino group having 2 to 5 carbon atoms in the alkanoyl moiety or a benzenesulphonylamino group, both of which may be substituted at the nitrogen atom by a $C_{1-3}$-alkyl group, a phthalimino or homophthalimino group, in which a carbonyl group in a phthalimino group may be replaced by a methylene group, a 5-, 6- or 7-membered alkyleneimino group in which a methylene group may be replaced by a carbonyl or sulphonyl group, a glutaric acid imino group in which the n-propylene group may be substituted by one or two $C_{1-3}$-alkyl groups or by a tetramethylene or pentamethylene group, a maleic acid imido group optionally mono- or disubstituted by a $C_{1-3}$-alkyl group or by a phenyl group, in which the substituents may be identical or different, a benzimidazol-2-yl group optionally substituted in the 1-position by a $C_{1-6}$-alkyl group or a $C_{3-7}$-cycloalkyl group, wherein the phenyl nucleus in a benzimidazol-2-yl group mentioned above may additionally be substituted by a fluorine atom or by a methyl or trifluoromethyl group, an imidazo[2,1-b]thiazol-6-yl, imidazo[1,2-a]pyridin-2-yl, 5,6,7,8-tetrahydro-imidazo[1,2-a]pyridin-2-yl, imidazo[1,2-a]pyrimidin-2-yl, imidazo[4,5-b]pyridin-2-yl, imidazo[4,5-c]pyridin-2-yl, imidazo[1,2-c]pyrimidin-2-yl, imidazo[1,2-a]pyrazin-2-yl, imidazo[1,2-b]-pyridazin-2-yl, imidazo[4,5-c]pyridin-2-yl, purin-8-yl, imidazo[4,5-b]pyrazin-2-yl, imidazo[4,5-c]pyridazin-2-yl or imidazo[4,5-d]pyridazin-2-yl group, a pyrrolidine, piperidine or pyridine ring bound via a carbon atom, wherein a phenyl group may be fused onto the pyridine ring via two adjacent carbon atoms and a methylene group adjacent to the N-atom in a pyrrolidine or piperidine ring may be replaced by a carbonyl or sulphonyl group, an imidazol-4-yl group optionally substituted in the 2-position by a $C_{1-6}$-alkyl group or by a phenyl group, and substituted in the 1-position by a $C_{1-7}$-alkyl group (which may be substituted in the 2-, 3-, 4-, 5-, 6- or 7-position by a carboxy, alkoxycarbonyl, aminocarbonyl, alkylaminocarbonyl, dialkylaminocarbonyl, morpholinocarbonyl, thiomorpholinocarbonyl or 1-oxidothiomorpholinocarbonyl group), by a $C_{2-4}$-alkyl group (substituted in the 2-, 3- or 4-position by a hydroxy, alkoxy or imidazol-1-yl group), by an alkyl group (substituted by a trifluoromethyl group, by a $C_{3-7}$-cycloalkyl group or by a phenyl group optionally mono- or disubstituted by fluorine or chlorine atoms or by trifluoromethyl, methyl or methoxy groups), by an alkyl group substituted by two phenyl groups, or by a $C_{3-7}$-cycloalkyl group, whilst unless otherwise specified the above-mentioned alkyl and alkoxy moieties may each contain 1 to 3 carbon atoms, a carboxy, aminocarbonyl, alkylaminocarbonyl or dialkylamino group in which each alkyl moiety may contain 1 to 6 carbon atoms, or a group which is metabolically converted in vivo into a carboxy group, or an $R_5$-$NR_4$-CO-$NR_3$- group wherein $R_3$ denotes a hydrogen atom, a $C_{1-5}$-alkyl group, a cyclohexyl or benzyl group, $R_4$ denotes a hydrogen atom, a $C_{1-6}$-alkyl group, an allyl, cyclohexyl, benzyl or phenyl group, $R_5$ denotes a hydrogen atom or a $C_{1-3}$-alkyl group or $R_4$ and $R_5$ together with the nitrogen atom between them denote an unbranched $C_{4-6}$-cycloalkyleneimino group or a morpholino group or $R_3$ and $R_4$ together denote a $C_{2-3}$-alkylene group, $R_a$ denotes a $C_{1-5}$-alkyl group, a $C_{3-5}$-cycloalkyl group, an alkoxy, alkylthio or alkylamino group each having 1 to 3 carbon atoms in each alkyl moiety, $R_b$ denotes a carboxy, cyano, hydroxysulphonyl, 1H-tetrazolyl, 1-triphenylmethyl-tetrazolyl or 2-triphenylmethyl-tetrazolyl group, a group which is metabolically converted in vivo into a carboxy group, an alkanecarbonylaminosulphonyl, benzoylaminosulphonyl, alkanesulphonylaminocarbonyl, trifluoromethanesulphonylaminocarbonyl or phenylsulphonylaminocarbonyl group, whilst in the above-mentioned groups the alkyl and alkoxy moieties may each contain 1 to 4 carbon atoms, and $R_c$ denotes an alkyl group, a $C_{3-6}$-cycloalkyl group or a phenyl group, which may be mono- or disubstituted by a fluorine, chlorine or bromine atom or by a hydroxy, alkoxy or alkyl group, wherein the substituents may be identical or different and the alkyl and alkoxy moieties mentioned in the above-mentioned groups may each contain 1 to 6 carbon atoms.

The expression "a group which is metabolically converted in vivo into a carboxy group" denotes, for example, the esters thereof of the formulae

-CO-OR',

-CO-O-(HCR")-O-CO-R''' and

-CO-O-(HCR")-O-CO-OR''' wherein

R' denotes a straight-chained or branched $C_{1-6}$-alkyl group, a $C_{5-7}$-cycloalkyl group, a benzyl, 1-phenylethyl, 2-phenylethyl, 3-phenylpropyl, methoxymethyl or cinnamyl group, R" denotes a hydrogen atom or a methyl group and R'" denotes a straight-chained or branched $C_{1-6}$-alkyl group, a $C_{5-7}$-cycloalkyl group, a phenyl, benzyl, 1-phenylethyl, 2-phenylethyl or 3-phenylpropyl group.

The new compounds of formula I above have valuable properties. Thus, the compounds of formula I wherein $R_b$ denotes a group which is metabolically converted in vivo into a carboxy group, a carboxy or 1H-tetrazolyl group, have particularly valuable pharmacological properties, being angiotensin-antagonists, especially angiotensin -II-antagonists. The other compounds of general formula I wherein $R_b$ denotes, for example, the cyano, 1-triphenylmethyl-tetrazolyl or 2-triphenylmethyltetrazolyl group, are valuable intermediate products for preparing the above-mentioned compounds.

The present invention thus relates to the new benzimidazol-1-yl, imidazo[4,5-b]pyridin-1-yl, imidazo[4,5-c]pyridin-1-yl, imidazo[4,5-b]pyridin-3-yl and imidazo[4,5-c]pyridin-3-yl-benzimidazolylmethyl derivatives of general formula I above, the mixtures of position isomers thereof and the salts thereof, particularly for pharmaceutical use, the acceptable salts thereof, and processes for preparing them.

The present invention further relates to new pharmaceutical compositions which contain one of the above-mentioned pharmacologically active compounds of general formula I or a corresponding physiologically acceptable salt and particularly for treating hypertension and cardiac insufficiency, and also for treating ischaemic peripheral circulatory disorders, myocardial ischaemia (angina), for preventing the progression of cardiac insufficiency after myocardial infarct, for treating diabetic nephropathy, glaucoma, gastrointestinal diseases, bladder diseases, for preventing atherosclerotic vascular changes and for preventing restenosis after surgical widening of vascular stenosis.

As examples of definitions of the groups $R_a$ to $R_b$ given hereinbefore $R_a$ may denote a methyl, ethyl, n-propyl, isopropyl, n-butyl, 1-methyl-n-propyl, 2-methyl-n-propyl, tert.butyl, n-pentyl, 1-methyl-1-butyl, 2-methyl-1-butyl, 3-methyl-1-butyl, 1,1-dimethyl-1-propyl, 2,2-dimethyl-1-propyl, cyclopropyl, cyclobutyl, cyclopentyl, methoxy, ethoxy, n-propoxy, isopropoxy, methylthio, ethylthio, n-propylthio, isopropylthio, methylamino, ethylamino, n-propylamino or isopropylamino group, $R_b$ may denote a hydroxycarbonyl, methoxycarbonyl, ethoxycarbonyl, n-propyloxycarbonyl, isopropyloxycarbonyl, n-butyloxycarbonyl, isobutyloxycarbonyl, tert.butyloxycarbonyl, n-pentyloxycarbonyl, isoamyloxycarbonyl, n-hexyloxycarbonyl, cyclopentyloxycarbonyl, cyclohexyloxycarbonyl, benzyloxycarbonyl, 1-phenylethyloxycarbonyl, 2-phenylethyloxycarbonyl, 3-phenylpropyloxycarbonyl, methoxymethoxycarbonyl, cinnamyloxycarbonyl, acetoxymethoxycarbonyl, propionyloxymethoxycarbonyl, n-butyryloxymethoxycarbonyl, isobutyryloxymethoxycarbonyl, n-pentanoyloxymethoxycarbonyl, isopentanoyloxymethoxycarbonyl, pivaloyloxymethoxycarbonyl, n-hexanoyloxymethoxycarbonyl, cyclopentanoyloxymethoxycarbonyl, cyclohexanoyloxymethoxycarbonyl, phenylacetoxymethoxycarbonyl, 2-phenylpropionyloxymethoxycarbonyl, 3-phenylpropionyloxymethoxycarbonyl, 4-phenylbutyryloxymethoxycarbonyl, benzoyloxymethoxycarbonyl, 1-acetoxyethoxycarbonyl, 1-propionyloxyethoxycarbonyl, 1-n-butyryloxyethoxycarbonyl, 1-isobutyryloxyethoxycarbonyl, 1-n-pentanoyloxyethoxycarbonyl, 1-isopentanoyloxyethoxycarbonyl, 1-pivaloyloxyethoxycarbonyl, 1-n-hexanoyloxyethoxycarbonyl, 1-cyclopentanoyloxyethoxycarbonyl, 1-cyclohexanoyloxyethoxycarbonyl, 1-phenylacetoxyethoxycarbonyl, 1-(2-phenylpropionyloxy)-ethoxycarbonyl, 1-(3-phenylpropionyloxy)-ethoxycarbonyl, 1-(4-phenylbutyryloxy)-ethoxycarbonyl, 1-benzoyloxyethoxycarbonyl, methoxycarbonyloxymethoxycarbonyl, ethoxycarbonyloxymethoxycarbonyl, n-propyloxycarbonyloxymethoxycarbonyl, isopropyloxycarbonyloxymethoxycarbonyl, n-butyloxycarbonyloxymethoxycarbonyl, isobutyloxycarbonyloxymethoxycarbonyl, tert.butyloxycarbonyloxymethoxycarbonyl, n-pentyloxycarbonyloxymethoxycarbonyl, isoamyloxycarbonyloxymethoxycarbonyl, n-hexyloxycarbonyloxymethoxycarbonyl, cyclopentyloxycarbonyloxymethoxycarbonyl, cyclohexyloxycarbonyloxymethoxycarbonyl, benzyloxycarbonyloxymethoxycarbonyl, 1-phenylethoxycarbonyloxymethoxycarbonyl, 2-phenylethoxycarbonyloxymethoxycarbonyl, 3-phenylpropyloxycarbonyloxymethoxycarbonyl, cinnamyloxycarbonyloxymethoxycarbonyl, 1-(methoxycarbonyloxy)-ethoxycarbonyl, 1-(ethoxycarbonyloxy)-ethoxycarbonyl, 1-(n-propyloxycarbonyloxy)-ethoxycarbonyl, 1-(isopropyloxycarbonyloxy)-ethoxycarbonyl, 1-(n-butyloxycarbonyloxy)-ethoxycarbonyl, 1-(isobutyloxycarbonyloxy)-ethoxycarbonyl, 1-(tert.butyloxycarbonyloxy)-ethoxycarbonyl, 1-(n-pentyloxycarbonyloxy)-ethoxycarbonyl, 1-(isoamyloxycarbonyloxy)-ethoxycarbonyl, 1-(n-hexyloxycarbonyloxy)-ethoxycarbonyl, 1-(cyclopentyloxycarbonyloxy)-ethoxycarbonyl, 1-(cyclohexyloxycarbonyloxy)-ethoxycarbonyl, 1-(benzyloxycarbonyloxy)-ethoxycarbonyl, 1-(1-phenylethoxycarbonyloxy)-ethoxycarbonyl, 1-(2-phenylethoxycarbonyloxy)-ethoxycarbonyl, 1-(3-phenylpropyloxycarbonyloxy)-ethoxycarbonyl, 1-(cinnamyloxycarbonyloxy)-ethoxycarbonyl, hydroxysulphonyl, cyano, 1H-tetrazolyl, 1-triphenylmethyl-tetrazolyl, 2-triphenylmethyltetrazolyl, trifluoromethanesulphonylaminocarbonyl, methanesulphonylaminocarbonyl, ethanesulphonylaminocarbonyl, n-propanesulphonylaminocarbonyl, isopropanesulphonylaminocarbonyl, phenylsulphonylaminocarbonyl, 4-fluorophenylsulphonylaminocarbonyl, 4-chlorophenylsulphonylaminocarbonyl, 4-bromophenylsulphonylaminocarbonyl, 4-methylphenylsulphonylaminocarbonyl, 4-methoxyphenylsulphonylaminocarbonyl, methylcarbonylaminosulphonyl, ethylcarbonylaminosulphonyl, n-propylcarbonylaminosulphonyl, n-butylcarbonylaminosulphonyl or benzoylaminosulphonyl group, $R_c$ may denote a methyl, ethyl, n-propyl, isopropyl, isobutyl, n-butyl, 1-methyl-n-propyl, 2-methyl-n-propyl, tert.butyl, n-pentyl, 1-methyl-n-butyl, 2-methyl-n-butyl, n-hexyl, 1-methyl-n-pentyl, 2-methyl-n-pentyl, 3-methyl-n-pentyl, cyclopropyl, cyclobutyl, cyclopentyl, cyclohexyl, phenyl, 2-fluoro-phenyl, 3-fluoro-phenyl, 4-fluoro-phenyl, 2-chloro-phenyl, 3-chloro-phenyl,4-chloro-phenyl, 2-bromo-phenyl, 3-bromo-phenyl, 4-bromophenyl, 2-methyl-phenyl, 3-methyl-phenyl, 4-methylphenyl, 2-ethyl-phenyl, 3-ethyl-phenyl, 4-ethyl-phenyl, 2-n-propyl-phenyl, 3-n-butyl-phenyl, 4-n-pentyl-phenyl, 2-hydroxy-phenyl, 3-hydroxy-phenyl, 4-hydroxy-phenyl, 2-methoxy-phenyl, 3-methoxy-phenyl, 4-methoxy-phenyl, 2-ethoxy-phenyl, 3-ethoxy-phenyl, 4-ethoxy-phenyl, 2-n-propoxy-phenyl, 3-n-butoxy-phenyl, 4-n-hexoxy-phenyl, 2,4-difluoro-phenyl, 2,5-dichloro-phenyl, 3,4-dibromophenyl, 2,4-dimethylphenyl, 3,4-dimethoxy-phenyl, 3,4-dihydroxy-phenyl or 2-chloro-5-methoxy-phenyl group, $R_1$ may denote a hydrogen, fluorine, chlorine or bromine atom or a methyl, ethyl, n-propyl, isopropyl or trifluoromethyl group, R₂ may denote a hydrogen atom, an acetylamino, propionylamino, butanoylamino, pentanoylamino, benzoylamino, N-acetyl-methylamino, N-propionylmethylamino, N-butanoyl-methylamino, N-pentanoylmethylamino, N-benzoylmethylamino, N-acetyl-ethylamino, N-propionyl-ethylamino, N-butanoyl-ethylamino, N-pentanoyl-ethylamino, N-benzoyl-ethylamino, N-acetylisopropylamino, N-propionyl-n-propylamino, N-butanoyl-n-propylamino, N-pentanoyl-isopropylamino, N-benzoylisopropylamino, 2-(imidazol-1-yl)-ethoxy, 3-(imidazol-1-yl)-propoxy, 4-(imidazol-1-yl)-butoxy, 5-(imidazol-1-yl)-pentoxy, 2-(benzimidazol-1-yl)-ethoxy, 3-(benzimidazol-1-yl)-propoxy, 4-(benzimidazol-1-yl)-butoxy, 5-(benzimidazol-1-yl)-pentoxy, 2-(tetrahydrobenzimidazol-1-yl)-ethoxy, 3-(tetrahydrobenzimidazol-1-yl)-propoxy, 4-(tetrahydrobenzimidazol-1-yl)-butoxy, 5-(tetrahydrobenzimidazol-1-yl)-pentoxy, carboxy, methoxycarbonyl, ethoxycarbonyl, isopropoxycarbonyl, pentoxycarbonyl, phthalimino, homophthalimino, 1-oxo-isoindolin-2-yl, pyrrolidino, piperidino, hexamethyleneimino, 2-oxo-pyrrolidino, 2-oxo-piperidino, 2-oxo-hexamethyleneimino, propanesultam-1-yl, butanesultam-1-yl, pentanesultam-1-yl, glutarimino, 3,3-tetramethylene-glutarimino, 3,3-pentamethyleneglutarimino, 2,2-dimethyl-glutarimino, 3-methylglutarimino, 3,3-dimethyl-glutarimino, 3-ethylglutarimino, 3-ethyl-3-methyl-glutarimino, 1,3-cyclopentanedicarboxylimino, 2,4-dimethyl-glutarimino, 2,4-di-n-propyl-glutarimino, maleic acid imido, 2-methyl-maleic acid imido, 2-phenyl-maleic acid imido, 2,3-dimethyl-maleic acid imido, 3-methyl-2-phenyl-maleic acid imido, 2,3-diphenyl-maleic acid amido, pyrrolidin-2-yl, pyrrolidin-2-on-5-yl, piperidin-2-yl, piperidin-2 on-1-yl, piperidin-2-on-6-yl, pyridin-2-yl, quinolin-2-yl, isoquinolin-1-yl, isoquinolin-3-yl, 1-methylimidazol-4-yl, 1-ethyl-imidazol-4-yl, 1-n-propyl-imidazol-4-yl, 1-isopropyl-imidazol-4-yl, 1-n-butyl-imidazol-4-yl, 1-isobutyl-imidazol-4-yl, 1-n-pentyl-imidazol-4-yl, 1-isoamyl-imidazol-4-yl, 1-n-hexyl-imidazol-4-yl, 1-n-hexyl-2-methyl-imidazol-4-yl, 1 -(1-methyl-n-pentyl )-imidazol-4-yl, 1-(1-ethyl-n-butyl) -imidazol-4-yl, 1-(1-methyl-n-hexyl)-imidazol-4-yl, 1-(1-ethyl-n-pentyl) -imidazol-4-yl, 1-(1-n-propyl-n-butyl) -imidazol-4-yl, 1-n-heptyl-imidazol-4-yl, 1-ethyl-2 -methyl-imidazol-4-yl, 1-n-propyl-2-methyl-imidazol-4-yl, 1-isopropyl-2-methyl-imidazol-4-yl, 1-n-butyl-2-methyl -imidazol-4-yl, 1-isobutyl-2-methyl-imidazol-4-yl, 1-n-pentyl-2-methyl-imidazol-4-yl, 1-isoamyl-2-methyl-imidazol-4-yl, 1-n-hexyl-2-methyl-imidazol-4-yl, 1-n-heptyl-2-methyl-imidazol-4-yl, 1-cyclopropylmethylimidazol-4-yl, 1-cyclobutylmethyl-imidazol-4-yl, 1-cyclopentylmethyl-imidazol-4-yl, 1-cyclohexylmethyl-imidazol-4-yl, 1-cycloheptylmethyl-imidazol-4-yl, 1-(2-cyclopropylethyl)-imidazol-4-yl, 1-(2-cyclobutylethyl)-imidazol-4-yl, 1-(2-cyclopentylethyl)-imidazol-4-yl, 1(2-cyclohexylethyl)-imidazol-4-yl, 1-(2-cycloheptylethyl)-imidazol-4-yl, 1-(3-cyclopropylpropyl)-imidazol-4-yl, 1-(3-cyclobutylpropyl)-imidazol-4-yl, 1-(3-cyclopentylpropyl)-imidazol-4-yl, 1-(3-cyclohexylpropyl)-imidazol-4-yl, 1-(3-cycloheptylpropyl)-imidazol-4-yl, 1-(2,2,2-trifluoroethyl)-imidazol-4-yl, 1-(3,3,3-trifluoropropyl)-imidazol-4-yl, 1-benzyl-imidazol-4-yl, 1-(2-phenylethyl)-imidazol-4-yl, 1-(3-phenylpropyl)-imidazol-4-yl, 1-(4-fluoro-benzyl)-imidazol-4-yl, 1-(4-chloro-benzyl)-imidazol-4-yl, 1-(3-chloro-benzyl)-imidazol-4-yl, 1-(4-trifluoromethyl-benzyl)-imidazol-4-yl, 1-(3-methyl-benzyl) -imidazol-4-yl, 1-(4-methylbenzyl)-imidazol-4-yl, 1-(3 -methoxy-benzyl)-imidazol-4-yl, 1-(4-methoxy-benzyl)-imidazol-4-yl, 1-(3,4-dimethoxy-benzyl)-imidazol-4-yl, 1-(3,5-dimethoxybenzyl)-imidazol -4-yl, 1-cyclopropylmethyl-2-methyl-imidazol-4-yl, 1-cyclobutylmethyl-2-methyl-imidazol-4-yl, 1-cyclopentylmethyl-2-methyl-imidazol-4-yl, 1-cyclohexylmethyl -2-methyl-imidazol-4-yl, 1-cycloheptylmethy 1-2-methyl-imidazol-4-yl, 1-(2-cyclopropylethyl)-2-methyl-imidazol-4-yl, 1-(2-cyclobutylethyl)-2-methyl-imidazol-4-yl, 1-(2-cyclopentylethyl)-2-methyl-imidazol-4-yl, 1-(2-cyclohexylethyl)-2-methyl-imidazol-4-yl, 1-(2-cycloheptylethyl)-2-methyl-imidazol-4-yl, 1-(3-cyclopropylpropyl)-2-methyl-imidazol-4-yl, 1-(3-cyclobutylpropyl)-2-methyl-imidazol-4-yl, 1-(3-cyclopentylpropyl)-2-methyl-imidazol-4-yl, 1-(3-cyclohexylpropyl)-2-methyl-imidazol-4-yl, 1-(3-cycloheptylpropyl)-2-methyl-imidazol-4-yl, 1-(2,2,2-trifluoroethyl) -2-methyl-imidazol-4-yl, 1-(3,3,3-trifluoropropyl) -2-methyl-imidazol-4-yl, 1-benzyl-2-methyl-imidazol-4-yl, 1-(2-phenylethyl) -2-methyl-imidazol-4-yl, 1-(3-phenyl-propyl)-2-methyl-imidazol-4-yl, 1-(4-fluoro-benzyl)-2-methyl-imidazol-4-yl, 1-(4-chloro-benzyl)-2-methyl-imidazol-4-yl, 1-(3 -chlorobenzyl)-2-methyl-imidazol-4-yl, 1-(4 -trifluoromethylbenzyl)-2-methyl-imidazol-4-yl, 1-(3-methyl-benzyl)-2-methyl-imidazol-4-yl, 1-(4-methyl-benzyl)-2-methyl-imidazol-4-yl, 1-(3-methoxy-benzyl)-2-methyl-imidazol-4-yl, 1-(4-methoxy-benzyl)-2-methyl-imidazol-4-yl, 1-(3,4-dimethoxy-benzyl)-2-methyl-imidazol-4-yl, 1-(3,5-dimethoxy-benzyl )-2-methyl-imidazol-4-yl, 1-carboxymethyl-imidazol-4-yl, 1-(2-carboxyethyl)-imidazol-4-yl, 1-(3-carboxypropyl) -imidazol-4-yl, 1-(4carboxybutyl)-imidazol-4-yl, 1-(5-carboxypentyl) -imidazol-4-yl, 1-(6-carboxyhexyl)-imidazol-4-yl, 1-(7carboxyheptyl)-imidazol-4-yl, 1-methoxycarbonylmethyl-imidazol-4-yl, 1-(2-methoxycarbonylethyl)-imidazol-4-yl, 1-(3-methoxycarbonylpropyl)-imidazol-4 -yl, 1-(4-methoxycarbonylbutyl)-imidazol-4-yl, 1-(5-methoxycarbonylpentyl)-imidazol-4-yl, 1-(6-methoxycarbonylhexyl)-imidazol-4-yl, 1-(7-methoxycarbonylheptyl)-imidazol-4-yl, 1-ethoxycarbonylmethyl-imidazol-4-yl, 1-(2-ethoxycarbonylethyl)-imidazol-4-yl, 1-(3-ethoxycarbonylpropyl)-imidazol-4-yl, 1-(4-ethoxycarbonylbutyl)-imidazol-4-yl, 1-(5-ethoxycarbonylpentyl)-imidazol-4-yl, 1-(6-ethoxycarbonylhexyl)-imidazol-4-yl, 1(7-ethoxycarbonylheptyl)-imidazol-4-yl, 1-n-propoxycarbonylmethyl-imidazol-4-yl, 1-(2-n-propoxycarbonylethyl)-imidazol-4-yl, 1-(3-n-propoxycarbonylpropyl)-imidazol-4-yl, 1-(4-n-propoxycarbonylbutyl)-imidazol-4-yl, 1-(5-n-propoxycarbonylpentyl)-imidazol-4-yl, 1-(6-n-propoxycarbonylhexyl)-imidazol-4-yl, 1-(7-n-propoxycarbonylheptyl)-imidazol-4-yl, 1-isopropoxycarbonylmethyl-imidazol-4-yl, 1-(2-isopropoxycarbonylethyl)-imidazol-4-yl, 1-(3-isopropoxycarbonylpropyl)-imidazol-4-yl, 1-(4-isopropoxycarbonylbutyl)-imidazol-4-yl, 1-(5-isopropoxycarbonylpentyl)-imidazol-4-yl, 1-(6-isopropoxycarbonylhexyl)-imidazol-4-yl, 1-(7-isopropoxycarbonylheptyl)-imidazol-4-yl, 1-aminocarbonylmethyl-imidazol-4-yl, 1-(2-aminocarbonylethyl)-imidazol-4-yl, 1-(3-aminocarbonylpropyl)-imidazol-4-yl, 1-(4-aminocarbonylbutyl)-imidazol-4-yl, 1-(5-aminocarbonylpentyl)-imidazol-4-yl, 1-(6-aminocarbonylhexyl) -imidazol-4-yl, 1-(7-aminocarbonylheptyl)-imidazol-4-yl, 1-methylaminocarbonylmethyl-imidazol-4-yl, 1-(2-methylaminocarbonylethyl)-imidazol-4-yl, 1-(3-methylaminocarbonylpropyl)-imidazol-4-yl, 1-(4-methylaminocarbonylbutyl) -imidazol-4-yl, 1-(5-methylaminocarbonylpentyl) -imidazol-4-yl, 1-(6-methylaminocarbonylhexyl)-imidazol-4-yl, 1-(7-methylaminocarbonylheptyl)-imidazol-4-yl, 1-ethylaminocarbonylmethyl-imidazol-4-yl, 1-(2-ethylaminocarbonylethyl)-imidazol-4-yl, 1-(3-ethylaminocarbonylpropyl)-imidazol-4-yl, 1-(4-ethylaminocarbonylbutyl)-imidazol-4-yl, 1-(5-ethylaminocarbonylpentyl)-imidazol-4-yl, 1-(6-ethylaminocarbonylhexyl)-imidazol-4-yl, 1-(7-ethylaminocarbonylheptyl)-imidazol-4-yl, 1-n-propylaminocarbonylmethyl-imidazol-4-yl, 1-(2-n-propylaminocarbonylethyl)-imidazol-4-yl, 1-(3-n-propylaminocarbonylpropyl)-imidazol-4-yl, 1-(4-n-propylaminocarbonylbutyl)-imidazol-4-yl, 1-(5-n-propylaminocarbonylpentyl)-imidazol-4-yl, 1-(6-n-propylaminocarbonylhexyl)-imidazol-4-yl, 1-(7-n-propylaminocarbonylheptyl)-imidazol-4-yl, 1-isopropylaminocarbonylmethyl-imidazol-4-yl, 1-(2-isopropylaminocarbonylethyl)-imidazol-4-yl, 1-(3-isopropylaminocarbonylpropyl)-imidazol-4-yl, 1-(4-isopropylaminocarbonylbutyl)-imidazol-4-yl, 1-(5-isopropylaminocarbonylpentyl)-imidazol-4-yl, 1-(6-isopropylaminocarbonylhexyl)-imidazol-4-yl, 1-(7-isopropylaminocarbonylheptyl)-imidazol-4-yl, 1-dimethylaminocarbonylmethyl-imidazol-4-yl, 1-(2-dimethylaminocarbonylethyl)-imidazol-4-yl, 1-(3-dimethylaminocarbonylpropyl)-imidazol-4-yl, 1-(4-dimethylaminocarbonylbutyl)-imidazol-4-yl, 1-(5-dimethylaminocarbonylpentyl)-imidazol-4-yl, 1-(6-dimethylaminocarbonylhexyl)-imidazol-4-yl, 1-(7-dimethylaminocarbonylheptyl)-imidazol-4-yl, 1-diethylaminocarbonylmethyl-imidazol-4-yl, 1-(2-diethylaminocarbonylethyl)-imidazol-4-yl, 1-(3-diethylaminocarbonylpropyl)-imidazol-4-yl, 1-(4-diethylaminocarbonylbutyl)-imidazol-4-yl, 1-(5-diethylaminocarbonylpentyl)-imidazol-4-yl, 1-(6-diethylaminocarbonylhexyl)-imidazol-4-yl, 1(7-diethylaminocarbonylheptyl)-imidazol-4-yl, 1-di-n-propylaminocarbonylmethyl-imidazol-4-yl, 1-(2-di-n-propylaminocarbonylethyl)-imidazol-4-yl, 1-(3-di-n-propylaminocarbonylpropyl)-imidazol-4-yl, 1-(4-di-n-propylaminocarbonylbutyl)-imidazol-4-yl, 1-(5-di-n-propylaminocarbonylpentyl)-imidazol-4-yl, 1-(6-di-n-propylaminocarbonylhexyl)-imidazol-4-yl, 1-(7-di-n-propylaminocarbonylheptyl)-imidazol-4-yl, 1-diisopropylaminocarbonylmethyl-imidazol-4-yl , 1-(2-diisopropylaminocarbonylethyl)-imidazol-4-yl, 1-(3-diisopropylaminocarbonylpropyl)-imidazol-4-yl, 1-(4-diisopropylaminocarbonylbutyl)-imidazol-4-yl, 1-(5-diisopropylaminocarbonylpentyl)-imidazol-4-yl, 1-(6-diisopropylaminocarbonylhexyl)-imidazol-4-yl, 1-(7-diisopropylaminocarbonylheptyl)-imidazol-4-yl, 1-morpholinocarbonylmethyl-imidazol-4-yl, 1-(2-morpholinocarbonylethyl)-imidazol-4-yl, 1-(3-morpholinocarbonylpropyl)-imidazol-4-yl, 1-(4-morpholinocarbonylbutyl)-imidazol-4-yl, 1-(5-morpholinocarbonylpentyl)-imidazol-4-yl, 1-(6-morpholinocarbonylhexyl)-imidazol-4-yl, 1-(7-morpholinocarbonylheptyl)-imidazol-4-yl, 1-thiomorpholinocarbonylmethyl-imidazol-4-yl, 1-(2-thiomorpholinocarbonylethyl)-imidazol-4-yl, 1-(3-thiomorpholinocarbonylpropyl)-imidazol-4-yl, 1-(4-thiomorpholinocarbonylbutyl)-imidazol-4-yl, 1-(5-thiomorpholinocarbonylpentyl)-imidazol-4-yl, 1-(6-thiomorpholinocarbonylhexyl)-imidazol-4-yl, 1-(7-thiomorpholinocarbonylheptyl)-imidazol-4-yl, 1-oxidothiomorpholinocarbonylmethyl-imidazol-4-yl, 1-(2-oxidothiomorpholinocarbonylethyl)-imidazol-4-yl, 1-(3-oxidothiomorpholinocarbonylpropyl)-imidazol-4-yl, 1-(4-oxidothiomorpholinocarbonylbutyl)-imidazol-4-yl, 1-(5-oxidothiomorpholinocarbonylpentyl)-imidazol-4-yl, 1-(6-oxidothiomorpholinocarbonylhexyl)-imidazol-4-yl, 1-(7-oxidothiomorpholinocarbonylheptyl)-imidazol-4-yl, 1-carboxymethyl-2-methyl-imidazol-4-yl, 1-(2-carboxyethyl)-2-methyl-imidazol-4-yl, 1-(3-carboxypropyl)-2-methyl-imidazol-4-yl, 1-(4-carboxybutyl)-2-methyl-imidazol-4-yl, 1-(5-carboxypentyl)-2-methyl-imidazol-4-yl, 1-(6-carboxyhexyl)-2-methyl-imidazol-4-yl, 1-(7-carboxyheptyl)-2-methyl-imidazol-4-yl, 1-methoxycarbonylmethyl-2-methyl-imidazol-4-yl, 1-(2-methoxycarbonylethyl)-2-methyl-imidazol-4-yl, 1-(3-methoxycarbonylpropyl)-2-methyl-imidazol-4-yl, 1-(4-methoxycarbonylbutyl)-2-methyl-imidazol-4-yl, 1-(5-methoxycarbonylpentyl)-2-methyl-imidazol-4-yl, 1-(6-methoxycarbonylhexyl)-2-methyl-imidazol-4-yl, 1-(7-methoxycarbonylheptyl)-2-methyl-imidazol-4-yl, 1-ethoxycarbonylmethyl-2-methyl-imidazol-4-yl, 1-(2-ethoxycarbonylethyl)-2-methyl-imidazol-4-yl, 1-(3-ethoxycarbonylpropyl)-2-methyl-imidazol-4-yl, 1-(4-ethoxycarbonylbutyl)-2-methyl-imidazol-4-yl, 1-(5-ethoxycarbonylpentyl)-2-methyl-imidazol-4-yl, 1-(6-ethoxycarbonylhexyl)-2-methyl-imidazol-4-yl, 1-(7-ethoxycarbonylheptyl)-2-methyl-imidazol-4-yl, 1-n-propoxycarbonylmethyl-2-methyl-imidazol-4-yl, 1-(2-n-propoxycarbonylethyl)-2-methyl-imidazol-4-yl, 1-(3-n-propoxycarbonylpropyl)-2-methyl-imidazol-4-yl, 1-(4-n-propoxycarbonylbutyl)-2-methyl-imidazol-4-yl, 1-(5-n-propoxycarbonylpentyl)-2-methyl-imidazol-4-yl, 1-(6 -n-1-(6-n-propoxycarbonylhexyl)-2-methyl-imidazol-4-yl, 1-(7-n-propoxycarbonylheptyl)-2-methyl-imidazol-4-yl, 1-isopropoxycarbonylmethyl-2-methyl-imidazol-4-yl, 1-(2-isopropoxycarbonylethyl)-2-methyl-imidazol-4-yl, 1-(3-isopropoxycarbonylpropyl)-2-methyl-imidazol-4-yl, 1-(4-isopropoxycarbonylbutyl)-2-methyl-imidazol-4-yl, 1-(5-isopropoxycarbonylpentyl)-2-methyl-imidazol-4-yl, 1-(6-isopropoxycarbonylhexyl)-2-methyl-imidazol-4-yl, 1-(7-isopropoxycarbonylheptyl)-2-methyl-imidazol-4-yl, 1-aminocarbonylmethyl-2-methyl-imidazol-4-yl, 1-(2-aminocarbonylethyl)-2-methyl-imidazol-4-yl, 1-(3-aminocarbonylpropyl)-2-methyl-imidazol-4-yl, 1-(4-aminocarbonylbutyl)-2-methyl-imidazol-4-yl, 1-(5-aminocarbonylpentyl)-2-methyl-imidazol-4-yl, 1-(6-aminocarbonylhexyl)-2-methyl-imidazol-4-yl, 1-(7-aminocarbonylheptyl)-2-methyl-imidazol-4-yl, 1-methylaminocarbonylmethyl-2-methyl-imidazol-4-yl, 1-(2-methylaminocarbonylethyl)-2-methyl-imidazol-4-yl, 1-(3-methylaminocarbonylpropyl)-2-methyl-imidazol-4-yl, 1-(4-methylaminocarbonylbutyl)-2-methyl-imidazol-4-yl, 1-(5-methylaminocarbonylpentyl)-2-methyl-imidazol-4-yl, 1-(6-methylaminocarbonylhexyl)-2-methyl-imidazol-4-yl, 1-(7-methylaminocarbonylheptyl)-2-methyl-imidazol-4-yl, 1-ethylaminocarbonylmethyl-2-methyl-imidazol-4-yl , 1-(2-ethylaminocarbonylethyl)-2-methyl-imidazol-4-yl , 1-(3-ethylaminocarbonylpropyl)-2-methyl-imidazol-4-yl, 1-(4-ethylaminocarbonylbutyl)-2-methyl-imidazol-4-yl, 1-(5-ethylaminocarbonylpentyl)-2-methyl-imidazol-4-yl, 1-(6-ethylaminocarbonylhexyl)-2-methyl-imidazol-4-yl, 1-(7-ethylaminocarbonylheptyl)-2-methyl-imidazol-4-yl, 1-n-propylaminocarbonylmethyl-2-methyl-imidazol-4-yl, 1-(2-n-propylaminocarbonylethyl)-2-methyl-imidazol-4-yl, 1-(3-n-propylaminocarbonylpropyl)-2-methyl-imidazol-4-yl, 1-(4-n-propylaminocarbonylbutyl)-2-methyl-imidazol-4-yl, 1-(5-n-propylaminocarbonylpentyl)-2-methyl-imidazol-4-yl, 1-(6-n-propylaminocarbonylhexyl)-2-methyl-imidazol-4-yl, 1-(7-n-propylaminocarbonylheptyl)-2-methyl-imidazol-4-yl, 1-isopropylaminocarbonylmethyl-2-methyl-imidazol-4-yl, 1-(2-isopropylaminocarbonylethyl)-2-methyl-imidazol-4-yl, 1-(3-isopropylaminocarbonylpropyl)-2-methyl-imidazol-4-yl, 1-(4-isopropylaminocarbonylbutyl)-2-methyl-imidazol-4-yl, 1-(5-isopropylaminocarbonylpentyl)-2-methyl-imidazol-4-yl, 1-(6- isopropylaminocarbonylhexyl)-2-methyl-imidazol-4-yl, 1-(7-isopropylaminocarbonylheptyl)-2-methyl-imidazol-4-yl, 1-dimethylaminocarbonylmethyl-2-methyl-imidazol-4-yl, 1-(2-dimethylaminocarbonylethyl)-2-methyl-imidazol-4-yl, 1-(3-dimethylaminocarbonylpropyl)-2-methyl-imidazol-4-yl, 1-(4-dimethylaminocarbonylbutyl)-2-methyl-imidazol-4-yl, 1-(5-dimethylaminocarbonylpentyl)-2-methyl-imidazol-4-yl, 1-(6-dimethylaminocarbonylhexyl)-2-methyl-imidazol-4-yl, 1-(7-dimethylaminocarbonylheptyl)-2-methyl-imidazol-4-yl, 1-diethylaminocarbonylmethyl-2-methyl-imidazol-4-yl, 1-(2-diethylaminocarbonylethyl)-2-methyl-imidazol-4-yl, 1-(3-diethylaminocarbonylpropyl)-2-methyl-imidazol-4-yl, 1-(4-diethylaminocarbonylbutyl)-2-methyl-imidazol-4-yl, 1-(5-diethylaminocarbonylpentyl)-2-methyl-imidazol-4-yl, 1-(6-diethylaminocarbonylhexyl)-2-methyl-imidazol-4-yl, 1-(7-diethylaminocarbonylheptyl)-2-methyl-imidazol-4-yl, 1-di-n-propylaminocarbonylmethyl-2-methyl-imidazol-4-yl, 1-(2-di-n-propylaminocarbonylethyl)-2-methyl-imidazol-4-yl, 1-(3-di-n-propylaminocarbonylpropyl)-2-methyl-imidazol-4-yl, 1-(4-di-n-propylaminocarbonylbutyl)-2-methyl-imidazol-4-yl, 1-(5-di-n-propylaminocarbonylpentyl)-2-methyl-imidazol-4-yl, 1-(6-di-n-propylaminocarbonylhexyl)-2-methyl-imidazol-4-yl, 1-(7-di-n-propylaminocarbonylheptyl)-2-methyl-imidazol-4-yl, 1-diisopropylaminocarbonylmethyl-2-methyl-imidazol-4-yl, 1-(2-diisopropylaminocarbonylethyl)-2-methyl-imidazol-4-yl, 1-(3-diisopropylaminocarbonylpropyl)-2-methyl-imidazol-4-yl, 1-(4-diisopropylaminocarbonylbutyl)-2-methyl-imidazol-4-yl, 1-(5-diisopropylaminocarbonylpentyl)-2-methyl-imidazol-4-yl, 1-(6-diisopropylaminocarbonylhexyl)-2-methyl-imidazol-4-yl, 1-(7-diisopropylaminocarbonylheptyl)-2-methyl-imidazol-4-yl, 1-morpholinocarbonylmethyl-2-methyl-imidazol-4-yl, 1-(2-morpholinocarbonylethyl)-2-methyl-imidazol-4-yl, 1-(3-morpholinocarbonylpropyl)-2-methyl-imidazol-4-yl, 1-(4-morpholinocarbonylbutyl)-2-methyl-imidazol-4-yl, 1-(5-morpholinocarbonylpentyl)-2-methyl-imidazol-4-yl, 1-(6-morpholinocarbonylhexyl)-2-methyl-imidazol-4-yl, 1-(7-morpholinocarbonylheptyl)-2-methyl-imidazol-4-yl, 1-thiomorpholinocarbonylmethyl-2-methyl-imidazol-4-yl, 1(2-thiomorpholinocarbonylethyl)-2-methyl-imidazol-4-yl, 1-(3-thiomorpholinocarbonylpropyl)-2-methyl-imidazol-4-yl, 1-(4-thiomorpholinocarbonylbutyl)-2-methyl-imidazol-4-yl, 1-(5-thiomorpholinocarbonylpentyl)-2-methylimidazol-4-yl, 1-(6-thiomorpholinocarbonylhexyl)-2-methyl-imidazol-4-yl, 1-(7-thiomorpholinocarbonylheptyl)-2-methyl-imidazol-4-yl, 1-oxidothiomorpholinocarbonylmethyl-2-methyl-imidazol-4-yl, 1-(2-oxidothiomorpholinocarbonylethyl)-2-methyl-imidazol-4-yl, 1-(3-oxidothiomorpholinocarbonylpropyl)-2-methyl-imidazol-4-yl, 1-(4-oxidothiomorpholinocarbonylbutyl)-2-methyl-imidazol-4-yl, 1-(5-oxidothiomorpholinocarbonylpentyl)-2-methyl-imidazol-4-yl, 1-(6-oxidothiomorpholinocarbonylhexyl)-2-methyl-imidazol-4-yl, 1-(7-oxidothiomorpholinocarbonylheptyl)-2-methyl-imidazol-4-yl, 1-(2-hydroxyethyl)-imidazol-4-yl, 1-(3-hydroxypropyl)-imidazol-4-yl, 1-(4-hydroxybutyl)-imidazol-4-yl, 1-(2-methoxyethyl)-imidazol-4-yl, 1-(3-methoxypropyl)-imidazol-4-yl, 1-(4-methoxybutyl)-imidazol-4-yl, 1-(2-ethoxyethyl)-imidazol-4-yl, 1-(3-ethoxypropyl)-imidazol-4-yl, 1-(4-ethoxybutyl)-imidazol-4-yl, 1-(2-n-propoxyethyl)-imidazol-4-yl, 1-(3-n-propoxypropyl)-imidazol-4-yl, 1-(4-n-propoxybutyl)-imidazol-4-yl, 1-(2-isopropoxyethyl)-imidazol-4-yl, 1(3-isopropoxypropyl)-imidazol-4-yl, 1-(4-isopropoxybutyl)-imidazol-4-yl, 1-(2-imidazol-1-yl-ethyl)-imidazol-4-yl, 1-(3-imidazol-1-yl-propyl)-imidazol-4-yl, 1-(4-imidazol-1-yl-butyl)-imidazol-4-yl, 1-(2,2-diphenyl-ethyl)-imidazol-4-yl, 1-(3,3-diphenyl-propyl)-imidazol-4-yl, 1-(4,4-diphenyl-butyl)-imidazol-4-yl, 1-(2-hydroxyethyl)-2-methyl-imidazol-4-yl, 1-(3-hydroxypropyl)-2-methyl-imidazol-4-yl, 1-(4-hydroxybutyl)-2-methyl-imidazol-4-yl, 1-(2-methoxyethyl)-2-methyl-imidazol-4-yl, 1-(3-methoxypropyl)-2-methyl-imidazol-4-yl, 1-(4-methoxybutyl)-2-methyl-imidazol-4-yl, 1-(2-ethoxyethyl)-2-methyl-imidazol-4-yl, 1-(3-ethoxypropyl)-2-methyl-imidazol-4-yl, 1-(4-ethoxybutyl)-2-methyl-imidazol-4-yl, 1-(2-n-propoxyethyl)-2-methyl-imidazol-4-yl, 1-(3-n-propoxypropyl)-2-methyl-imidazol-4-yl, 1-(4-n-propoxybutyl)-2-methyl-imidazol-4-yl, 1-(2-isopropoxyethyl)-2-methyl-imidazol-4-yl, 1-(3-isopropoxypropyl)-2-methyl-imidazol-4-yl, 1-(4-isopropoxybutyl)-2-methyl-imidazol-4-yl, 1-(2-imidazol-1-yl-ethyl) -2-methyl-imidazol-4-yl, 1-(3-imidazol-1-yl-propyl)-2-methyl-imidazol-4-yl, 1-(4-imidazol-1-yl-butyl)-2-methyl-imidazol-4-yl, 1-(2,2-diphenyl-ethyl)-2-methyl-imidazol-4-yl, 1-(3,3-diphenyl-propyl) -2-methyl-imidazol-4-yl, 1-(4,4-diphenyl-butyl) -2-methyl-imidazol-4-yl, benzimidazol-2-yl, 1-methylbenzimidazol-2-yl, 1-ethylbenzimidazol-2-yl, 1-n-propylbenzimidazol-2-yl, 1-isopropylbenzimidazol-2-yl, 1-n-butylbenzimidazol-2-yl, 1-isobutylbenzimidazol-2-yl, 1-n-pentylbenzimidazol-2-yl, 1-n-hexylbenzimidazol-2-yl, 1-cyclopropylbenzimidazol-2-yl, 1-cyclobutylbenzimidazol-2-yl, 1-cyclopentylbenzimidazol-2-yl, 1-cyclohexylbenzimidazol-2-yl, 1,5-dimethyl-benzimidazol-2-yl, 1,6-dimethyl-benzimidazol-2-yl, 1,4-dimethyl-benzimidazol-2-yl, 5-fluoro-1-methyl-benzimidazol-2-yl, 6-fluoro-1-methyl-benzimidazol-2-yl, 5-trifluoromethyl-benzimidazol-2-yl, 5-trifluoromethyl-1-methyl-benzimidazol-2-yl, imidazo[1,2-a]pyridin-2-yl, 5,6,7,8-tetrahydroimidazo[1,2-a]pyrimidin-2-yl, imidazo[1,2-a]pyrimidin-2-yl, imidazo[4,5-b]pyridin-2-yl, imidazo[4,5-c]pyridin-2-yl, imidazo[2,1-b]thiazol-6-yl, imidazo[1,2-c]pyrimidin -2-yl, imidazo[1,2-a]pyrazin-2-yl, imidazo[1,2-b]-pyridazin-2-yl, imidazo[4,5-c]pyridin-2-yl, purin-8-yl, imidazo[4,5-b]pyrazin-2-yl, imidazo[4,5-c]pyridazin-2-yl, imidazo[4,5-d]pyridazin-2-yl, 4,5-dihydro-2H-pyridazin-3-on-6-yl, 2-methyl-4,5-dihydro-2H-pyridazin-3-on-6-yl, 2-benzyl-4,5-dihydro-2H-pyridazin-3-on-6-yl, 2H-pyridazin-3-on-6-yl, 2-methyl-pyridazin-3-on-6-yl, 2-benzyl-pyridazin-3-on-6-yl, aminocarbonylamino, methylaminocarbonylamino, dimethylaminocarbonylamino, N-methylaminocarbonyl-methylamino, N-(dimethylaminocarbonyl)-methylamino, N-dimethylaminocarbonylethylamino, N-dimethylaminocarbonyl-isopropylamino, N-(dimethylaminocarbonyl)-n-pentylamino, N-methylaminocarbonyl-ethylamino, N-methylaminocarbonyl-n-pentylamino, N-methylaminocarbonyl-cyclohexylamino, ethylaminocarbonylamino, N-ethylaminocarbonylmethylamino, N-ethylaminocarbonyl-ethylamino, N-ethylaminocarbonyl-cyclohexylamino, diethylaminocarbonylamino, N-(diethylaminocarbonyl)-methylamino, N-(diethylaminocarbonyl)-ethylamino, N-(diethylaminocarbonyl)-n-butylamino, isopropylaminocarbonylamino, N-isopropylaminocarbonyl-methylamino, n-butylaminocarbonylamino, N-(n-butylaminocarbonyl)-methylamino, N-(n-butylaminocarbonyl)-ethylamino, N-(n-butylaminocarbonyl)-isopropylamino, N-(n-butylaminocarbonyl)-n-butylamino, N-(n-butylaminocarbonyl)-cyclohexylamino, N-(di-(n-butyl)-aminocarbonyl)-amino, N-(di-(n-butyl)-aminocarbonyl)-methylamino, N-(di-(n-butyl) -aminocarbonyl)-ethylamino, N-(di-(n-butyl) -aminocarbonyl)-n-butylamino, N-(n-pentylaminocarbonyl)-methylamino, N-(n-pentylaminocarbonyl)-ethylamino, N-(n-hexylaminocarbonyl)-ethylamino, n-hexylaminocarbonylamino, N-(n-hexylaminocarbonyl)-n-butylamino, N-(n-hexylaminocarbonyl)-n-pentylamino, N-(n-hexylaminocarbonyl)-cyclohexylamino, di-(n-hexyl)aminocarbonylamino, N-(di-(n-hexyl)-aminocarbonyl)methylamino, N-((n-hexyl)-methylaminocarbonyl)-amino, cyclohexylaminocarbonylamino, N-cyclohexylaminocarbonylmethylamino, N-cyclohexylaminocarbonyl-ethylamino, N-cyclohexylaminocarbonyl-n-butylamino, N-cyclohexylaminocarbonyl-isobutylamino, N-cyclohexylaminocarbonyl-n-pentylamino, N-cyclohexylaminocarbonyl-cyclohexylamino, N-(ethylcyclohexylaminocarbonyl)-methylamino, N-(propylcyclohexylaminocarbonyl)-methylamino, N-(n-butylcyclohexylaminocarbonyl)-methylamino, allylaminocarbonylamino, benzylaminocarbonylamino, N-benzylaminocarbonyl-isobutylamino, phenylaminocarbonylamino, pyrrolidinocarbonylamino, pyrrolidinocarbonyl -methylamino, piperidinocarbonylamino, hexamethyleneiminocarbonylamino, morpholinocarbonylamino, 3,4,5,6-tetrahydro-2-pyrimidon-1-yl, 3-methyl -3,4,5,6-tetrahydro-2-pyrimidon-1-yl, 3-ethyl-3,4,5,6 -tetrahydro-2-pyrimidon-1-yl, 3-n-propyl-3,4,5,6 -tetrahydro-2-pyrimidon-1-yl, 3-isopropyl-3,4,5,6 -tetrahydro-2-pyrimidon-1-yl, hydroxycarbonyl, methoxycarbonyl, ethoxycarbonyl, n-propyloxycarbonyl, isopropyloxycarbonyl, n-butyloxycarbonyl, isobutyloxycarbonyl, tert.butyloxycarbonyl, n-pentyloxycarbonyl, isoamyloxycarbonyl, n-hexyloxycarbonyl, cyclopentyloxycarbonyl, cyclohexyloxycarbonyl, benzyloxycarbonyl, 1-phenylethyloxycarbonyl, 2-phenylethyloxycarbonyl, 3-phenylpropyloxycarbonyl, methoxymethoxycarbonyl, cinnamyloxycarbonyl, acetoxymethoxycarbonyl, propionyloxymethoxycarbonyl, n-butyryloxymethoxycarbonyl, isobutyryloxymethoxycarbonyl, n-pentanoyloxymethoxycarbonyl, isopentanoyloxymethoxycarbonyl, pivaloyloxymethoxycarbonyl, n-hexanoyloxymethoxycarbonyl, cyclopentanoyloxymethoxycarbonyl, cyclohexanoyloxymethoxycarbonyl, phenylacetoxymethoxycarbonyl, 1-phenylpropionyloxymethoxycarbonyl, 2-phenylpropionyloxymethoxycarbonyl, 3-phenylbutyryloxymethoxycarbonyl, benzoyloxymethoxycarbonyl, 1-acetoxyethoxycarbonyl, 1-propionyloxyethoxycarbonyl, 1-n-butyryloxyethoxycarbonyl, 1-isobutyryloxyethoxycarbonyl, 1-n-pentanoyloxyethoxycarbonyl, 1-isopentanoyloxyethoxycarbonyl, 1-pivaloyloxyethoxycarbonyl, 1-n-hexanoyloxyethoxycarbonyl, 1-cyclopentanoyloxyethoxycarbonyl, 1-cyclohexanoyloxyethoxycarbonyl, 1-phenylacetoxyethoxycarbonyl, 1-(1-phenylpropionyloxy)-ethoxycarbonyl, 1-(2-phenylpropionyloxy)-ethoxycarbonyl, 1-(3-phenylbutyryloxy)-ethoxycarbonyl, 1-benzoyloxyethoxycarbonyl, methoxycarbonyloxymethoxycarbonyl, ethoxycarbonyloxymethoxycarbonyl, n-propyloxycarbonyloxymethoxycarbonyl, isopropyloxycarbonyloxymethoxycarbonyl, n-butyloxycarbonyloxymethoxycarbonyl, isobutyloxycarbonyloxymethoxycarbonyl, tert.butyloxycarbonyloxymethoxycarbonyl, n-pentyloxycarbonyloxymethoxycarbonyl, isoamyloxycarbonyloxymethoxycarbonyl, n-hexyloxycarbonyloxymethoxycarbonyl, cyclopentyloxycarbonyloxymethoxycarbonyl, cyclohexyloxycarbonyloxymethoxycarbonyl, benzyloxycarbonyloxymethoxycarbonyl, 1-phenylethoxycarbonyloxymethoxycarbonyl, 2-phenylethoxycarbonyloxymethoxycarbonyl, 3-phenylpropyloxycarbonyloxymethoxycarbonyl, cinnamyloxycarbonyloxymethoxycarbonyl, 1-(methoxycarbonyloxy)ethoxycarbonyl, 1-(ethoxycarbonyloxy)-ethoxycarbonyl, 1-(n-propyloxycarbonyloxy)-ethoxycarbonyl, 1-(isopropyloxycarbonyloxy)-ethoxycarbonyl, 1-(n-butyloxycarbonyloxy)-ethoxycarbonyl, 1-(isobutyloxycarbonyloxy)-ethoxycarbonyl, 1-(tert.butyloxycarbonyloxy)-ethoxycarbonyl, 1-(n-pentyloxycarbonyloxy)-ethoxycarbonyl, 1-(isoamyloxycarbonyloxy)-ethoxycarbonyl, 1-(n-hexyloxycarbonyloxy)-ethoxycarbonyl, 1-(cyclopentyloxycarbonyloxy)-ethoxycarbonyl, 1-(cyclohexyloxycarbonyloxy)-ethoxycarbonyl, 1-(benzyloxycarbonyloxy)ethoxycarbonyl, 1-(1-phenylethoxycarbonyloxy)ethoxycarbonyl, 1-(2-phenylethoxycarbonyloxy)ethoxycarbonyl, 1-(3-phenylpropyloxycarbonyloxy)ethoxycarbonyl, 1-(cinnamyloxycarbonyloxy)ethoxycarbonyl, aminocarbonyl, methylaminocarbonyl, ethylaminocarbonyl, n-propyl-aminocarbonyl, isopropylaminocarbonyl, dimethylaminocarbonyl, diethylaminocarbonyl, di-n-propylaminocarbonyl, diisopropylaminocarbonyl, N-methyl-ethylaminocarbonyl or N-ethyl-isopropylaminocarbonyl group.

Preferred compounds of the general formula I above are those wherein

A denotes a 1,4-butadienylene group substituted by the groups $R_1$ and $R_2$ and wherein additionally the methine group in position 7 of the benzimidazole thus formed may be replaced by a nitrogen atom, wherein $R_1$ denotes a hydrogen atom or in the 4-position a fluorine, chlorine or bromine atom, a trifluoromethyl group or a $C_{1-3}$-alkyl group and $R_2$ denotes a hydrogen atom, a $C_{1-3}$-alkyl group, in the 6-position an alkanoylamino group having 2 to 5 carbon atoms in the alkanoyl moiety or a benzenesulphonylamino group, both of which may be substituted at the nitrogen atom by a $C_{1-3}$-alkyl group, in the 6-position a phthalimino or homophthalimino group, in which a carbonyl group in a phthalimino group may be replaced by a methylene group, in the 6-position a 5-, 6- or 7-membered alkyleneimino group in which a methylene group is replaced by a carbonyl or sulphonyl group, in the 6-position a maleic acid imido group optionally mono- or disubstituted by a $C_{1-3}$-alkyl group or by a phenyl group, wherein the substituents may be identical or different, in the 6-position a benzimidazol-2-yl group optionally substituted in the 1-position by a $C_{1-6}$-alkyl group or by a $C_{3-7}$-cycloalkyl group, wherein the phenyl nucleus in a benzimidazol-2-yl group as mentioned above may additionally be substituted by a fluorine atom or by a methyl or trifluoromethyl group; an imidazo[2,1-b]thiazol-6-yl, imidazo[1,2-a]pyridin-2-yl, 5,6,7,8-tetrahydro-imidazo[1,2-a]pyridin-2-yl, imidazo[1,2-a]pyrimidin-2-yl or imidazo[4,5-b]pyridin-2-yl group, in the 6-position an imidazol-4-yl group which may be substituted in the 1-position by a $C_{1-7}$-alkyl group (which may be substituted in the 2-, 3-, 4-, 5-, 6- or 7-position by a carboxy, alkoxycarbonyl, aminocarbonyl, alkylaminocarbonyl, dialkylaminocarbonyl, morpholinocarbonyl, thiomorpholinocarbonyl or 1-oxidothiomorpholinocarbonyl group), by a $C_{2-4}$-alkyl group (substituted in the 2-, 3- or 4-position by a hydroxy, alkoxy or imidazol-1-yl group), by an alkyl group (which is substituted by a trifluoromethyl group, by a $C_{3-7}$-cycloalkyl group or by a phenyl group optionally mono- or disubstituted by fluorine or chlorine atoms or by trifluoromethyl, methyl or methoxy groups), by an alkyl group substituted by two phenyl groups, or by a $C_{3-7}$-cycloalkyl group, whilst unless otherwise specified the above-mentioned alkyl and alkoxy moieties may each contain 1 to 3 carbon atoms, in the 7-position a carboxy, aminocarbonyl, alkylaminocarbonyl or dialkylamino group wherein each alkyl moiety may contain 1 to 6 carbon atoms, or a group which is metabolically converted in vivo into a carboxy group, or in the 6-position an $R_5$-$NR_4$-CO-$NR_3$- group wherein $R_3$ denotes a hydrogen atom, a $C_{1-5}$-alkyl group, a cyclohexyl or benzyl group, $R_4$ denotes a hydrogen atom, a $C_{1-6}$-alkyl group, an allyl, cyclohexyl, benzyl or phenyl group, $R_5$ denotes a hydrogen atom or a $C_{1-3}$-alkyl group or $R_4$ and $R_5$ together with the nitrogen atom between them denote an unbranched $C_{4-6}$-cycloalkyleneimino group or a morpholino group or $R_3$ and $R_4$ together denote a $C_{2-3}$-alkylene group, $R_a$ denotes a $C_{2-4}$-alkyl group, a $C_{3-4}$-cycloalkyl group or a $C_{2-3}$-alkoxy group, $R_b$ denotes a group which is metabolically converted in vivo into a carboxy group, or $R_b$ denotes a carboxy or 1H-tetrazolyl group and $R_c$ denotes a $C_{1-3}$-alkyl group, a $C_{3-6}$-cycloalkyl group or a phenyl group, the mixtures of position isomers thereof and the salts thereof.

Particularly preferred compounds of general formula I above are those wherein

A denotes a 1,4-butadienylene group in which the methine group in positions 4 and 6 of the benzimidazole thus formed are substituted by methyl groups and the methine group in position 7 is replaced by a nitrogen atom, or A denotes a 1,4-butadienylene group which is substituted by the groups $R_1$ and $R_2$, wherein $R_1$ denotes a hydrogen atom or in the 4-position a methyl group and $R_2$ in the 6-position denotes a 1-methyl-benzimidazol-2-yl group, $R_a$ denotes a $C_{2-4}$-n-alkyl group, $R_b$ denotes a carboxy or 1H-tetrazolyl group and $R_c$ denotes a $C_{1-3}$-alkyl group, a $C_{3-6}$-cycloalkyl group or a phenyl group, the mixtures of position isomers thereof and the salts thereof.

According to the invention the new compounds are obtained by the following methods:

a) reacting a benzimidazole of general formula

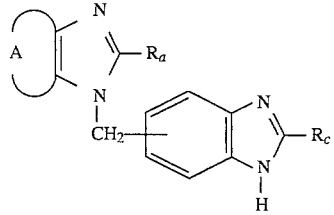

(II)

wherein $R_a$, $R_c$ and A are as hereinbefore defined, with a compound of general formula $$Z_1\text{-}CH_2\text{-}R_b \quad \text{(III)}$$

wherein $R_b$ has the meanings given hereinbefore with the exception of the 1H-tetrazolyl group and $Z_1$ denotes a nucleophilic leaving group such as a halogen atom, e.g. a chlorine, bromine or iodine atom, or a substituted sulphonyloxy group, e.g. a methanesulphonyloxy, phenylsulphonyloxy or p-toluenesulphonyloxy group, and optionally with subsequent cleaving of a 1-triphenylmethyl group from a triphenylmethyl-tetrazolyl compound thus obtained or hydrolysis of an ester thus obtained.

The reaction is conveniently carried out in a solvent or mixture of solvents such as methylene chloride, diethylether, tetrahydrofuran, dioxane, dimethylsulphoxide, dimethylformamide or benzene, optionally in the presence of an acid binding agent such as sodium carbonate, potassium carbonate, sodium hydroxide, sodium hydride, potassium tert.-butoxide, triethylamine or pyridine, whilst the latter two may simultaneously also be used as solvent, preferably at temperatures between 0° and 100° C., e.g. at temperatures between ambient temperature and 50° C.

The subsequent cleaving of a triphenylmethyl group is preferably carried out in the presence of a hydrogen halide, preferably in the presence of hydrogen chloride, in the presence of a base such as sodium hydroxide or alcoholic ammonia in a suitable solvent such as methylene chloride, methanol, methanol/ammonia, ethanol or isopropanol at temperatures between 0° and 100° C., but preferably at ambient temperature or, if the reaction is carried out in the presence of alcoholic ammonia, at elevated temperatures, e.g. at temperatures between 100° and 150° C., preferably at temperatures between 120° and 140° C.

The subsequent hydrolysis is conveniently carried out either in the presence of an acid such as hydrochloric acid, sulphuric acid, phosphoric acid, trichloroacetic acid or trifluoroacetic acid, in the presence of a base such as sodium hydroxide or potassium hydroxide, in a suitable solvent such as water, water/methanol, ethanol, water/ethanol, water/isopropanol or water/dioxane, at temperatures between −10° C. and 120° C., e.g. at temperatures between ambient temperature and the boiling temperature of the reaction mixture.

The reaction preferably produces a mixture of the 1- and 3-isomers which may subsequently, if desired, be resolved into the corresponding 1- and 3-isomers, preferably by chromatography using a carrier such as silica gel or aluminium oxide.

b) In order to prepare a compound of general formula I wherein $R_b$ denotes a carboxy group:

Converting a compound of general formula

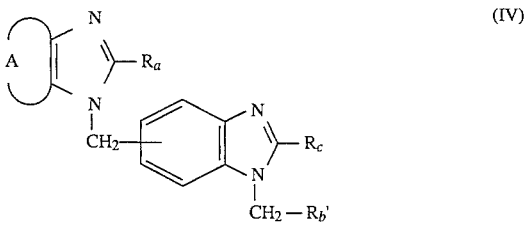

(IV)

wherein $R_a$, $R_c$ and A are as hereinbefore defined and $R_b'$ denotes a group which can be converted into a carboxy group by hydrolysis, thermolysis or hydrogenolysis, into a corresponding carboxy compound.

For example, functional derivatives of the carboxy group such as unsubstituted or substituted amides, esters, thiolesters, orthoesters, iminoethers, amidines or anhydrides, a nitrile group or a tetrazolyl group may be converted into a carboxy group by hydrolysis, esters with tertiary alcohols, e.g. a tert.butylester, may be converted into a carboxy group by thermolysis and esters with aralkanols, e.g. a benzylester, may be converted into a carboxy group by hydrogenolysis.

The hydrolysis is conveniently carried out in the presence of an acid such as hydrochloric acid, sulphuric acid, phosphoric acid, trichloroacetic acid or trifluoroacetic acid, or in the presence of a base such as sodium hydroxide or potassium hydroxide, in a suitable solvent such as water, water/methanol, ethanol, water/ethanol, water/isopropanol or water/dioxane, at temperatures between −10° C. and 120° C., e.g. at temperatures between ambient temperature and the boiling temperature of the reaction mixture. When hydrolysis is carried out in the presence of an organic acid such as trichloroacetic acid or trifluoroacetic acid, any alcoholic hydroxy groups present may optionally be simultaneously converted into a corresponding acyloxy group such as a trifluoroacetoxy group.

If $R_b'$ in a compound of general formula IV represents a cyano or aminocarbonyl group, these groups may also be converted into a carboxy group with a nitrite, e.g. sodium nitrite, in the presence of an acid such as sulphuric acid, which may also be simultaneously used as solvent, at temperatures between 0° and 50° C.

If $R_b'$ in a compound of general formula IV represents, for example, a tert.-butyloxycarbonyl group, the tert.butyl group may also be thermally cleaved, optionally in an inert solvent such as methylene chloride, chloroform, benzene, toluene, tetrahydrofuran or dioxane and preferably in the presence of a catalytic amount of an acid such as p-toluenesulphonic acid, sulphuric acid, phosphoric acid or polyphosphoric acid, preferably at the boiling temperature of the solvent used, e.g. at temperatures between 40° C. and 100° C.

If $R_b'$ in a compound of general formula IV represents, for example, a benzyloxycarbonyl group, the benzyl group may also be hydrogenolytically cleaved in the presence of a hydrogenation catalyst such as palladium/charcoal in a suitable solvent such as methanol, ethanol, ethanol/water, glacial acetic acid, ethyl acetate, dioxane or dimethylformamide, preferably at temperatures between 0° and 50° C., e.g. at ambient temperature, and under a hydrogen pressure of 1 to 5 bar. During hydrogenolysis, other groups may be reduced at the same time, e.g. a nitro group to an amino group, a benzyloxy group to a hydroxy group, a vinylidene group to the corresponding alkylidene group or a cinnamic acid group to a corresponding phenyl-propionic acid group, or they may be replaced by hydrogen atoms, e.g. a halogen by a hydrogen atom.

c) In order to prepare a compound of general formula I wherein $R_b$ denotes a 1H-tetrazolyl group:

Cleaving a protective group from a compound of general formula

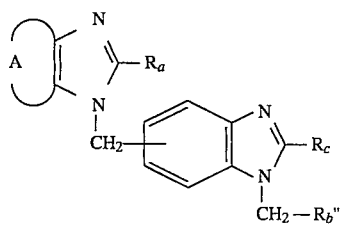

(V)

wherein $R_a$, $R_c$ and A are as hereinbefore defined and $R_b''$ denotes a 1H-tetrazolyl group protected in the 1- or 2-position by a protecting group.

Suitable protecting groups include, for example, the β-cyanoethyl, triphenylmethyl, tributyl tin or triphenyl tin groups.

The cleaving of a protective group used is preferably carried out in the presence of a hydrohalic acid, preferably in the presence of hydrochloric acid, in the presence of a base such as sodium hydroxide or alcoholic ammonia, in a suitable solvent such as methylene chloride, methanol, methanol/ammonia, ethanol or isopropanol, at temperatures between 0° and 100° C., but preferably at ambient temperature or, if the reaction is carried out in the presence of alcoholic ammonia, at elevated temperatures, e.g. at temperatures between 100° and 150° C., preferably at temperatures between 120° and 140° C.

d) In order to prepare a compound of general formula I wherein $R_b$ denotes a 1H-tetrazolyl group:

Reacting a compound of general formula

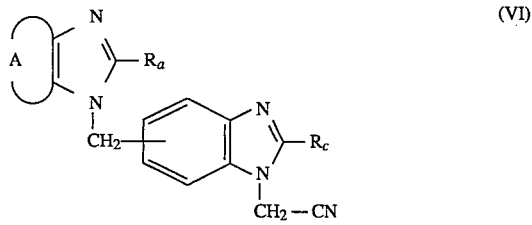

(VI)

wherein $R_a$, $R_c$ and A are as hereinbefore defined, with hydrazoic acid or the salts thereof.

The reaction is preferably carried out in a solvent such as benzene, toluene or dimethylformamide, at temperatures between 80° and 150° C., preferably at 125° C. Conveniently, either the hydrazoic acid is liberated during the reaction from an alkali metal azide, e.g. from sodium azide, in the presence of a weak acid such as ammonium chloride, or a tetrazolide salt obtained in the reaction mixture during the reaction with a salt of hydrazoic acid, preferably with aluminium azide or tributyl tin azide, which is also preferably produced in the reaction mixture by reacting aluminium chloride or tributyl tin chloride with an alkali metal azide such as sodium azide, is subsequently liberated by acidification with a dilute acid such as 2N hydrochloric acid or 2N sulphuric acid.

e) In order to prepare a compound of general formula I wherein $R_2$ denotes an $R_5$-$NR_4$-$CONR_3$- group:

Reacting a compound of general formula

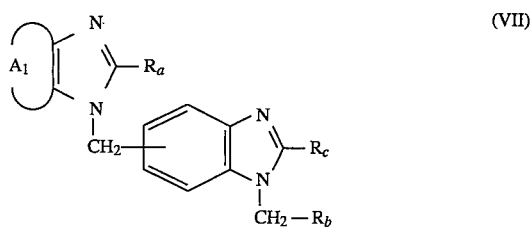

(VII)

with a compound of general formula

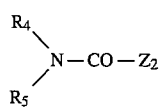

(VIII)

wherein $R_a$ to $R_c$, $R_4$ and $R_5$ are as hereinbefore defined, $A_1$ denotes a 1,4-butadienylene group which is substituted by $R_1$ and by an $R_3NH$-group, wherein $R_1$ and $R_3$ are as hereinbefore defined, and $Z_a$ denotes a nucleophilic leaving group such as a chlorine or bromine atom or $Z_2$ and $R_5$ together denote a nitrogen-carbon bond.

The reaction is conveniently carried out in a solvent or mixture of solvents such as dichloromethane, chloroform, diethylether, tetrahydrofuran, dioxane, dimethylformamide, dimethylsulphoxide, pyridine, benzene or toluene, at temperatures between 0° and 150° C., but preferably at temperatures between 50° and 120° C.

f) In order to prepare a compound of general formula I wherein $R_2$ denotes an alkanoylamino group having 2 to 5 carbon atoms in the alkanoyl moiety or a benzenesulphonylamino group, both of which may be substituted at the nitrogen atom by a $C_{1-3}$-alkyl group, or a phthalimino or homophthalimino group wherein a carbonyl group in a phthalimino group may be replaced by a methylene group, a 5-, 6- or 7-membered alkyleneimino group in which a methylene group is replaced by a carbonyl or sulphonyl group, a glutaric acid imino group in which the n-propylene group may be substituted by one or two $C_{1-3}$-alkyl groups or by a tetramethylene or pentamethylene group, or a maleic acid imido group optionally mono- or disubstituted by a $C_{1-3}$-alkyl group or by a phenyl group, wherein the substituents may be identical or different:

Reacting a compound of general formula

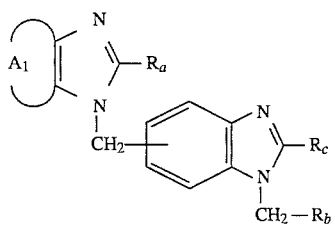
(VII)

with a compound of general formula

 (IX)

wherein $R_a$ to $R_c$ are as hereinbefore defined, $A_1$ denotes a 1,4-butadienylene group which is substituted by $R_1$ and by an $R_3NH-$ group, wherein $R_1$ and $R_3$ are as hereinbefore defined, $Z_3$ denotes a hydroxy group or a nucleophilic leaving group such as a halogen atom, e.g. a chlorine or bromine atom, U denotes a carbonyl or sulphonyl group and $R_6$ denotes a $C_{1-4}$-alkyl group, a phenyl, o-hydroxycarbonylphenyl, o-hydroxycarbonylphenylmethyl or o-hydroxycarbonylmethylphenyl group, a 3-hydroxycarbonylpropyl group optionally substituted by one or two $C_{1-3}$-alkyl groups or by a tetramethylene or pentamethylene group, or a 2-hydroxycarbonylethenyl group optionally mono- or disubstituted by a $C_{1-3}$-alkyl group or by a phenyl group, wherein the substituents may be identical or different, or $R_3$ and $R_6$ together denote an n-propylene, n-butylene or n-pentylene group, or, if $Z_3$ denotes a hydroxy group, with the reactive derivatives thereof such as the acid halides, acid anhydrides or acid esters thereof.

Examples of reactive derivatives of a compound of formula IX include the esters thereof, such as the methyl, ethyl or benzyl esters, the thioesters thereof such as the methylthio or ethylthio esters, the halides thereof such as the acid chloride, the anhydrides or imidazolides thereof and the orthoesters thereof.

The reaction is expediently carried out in a solvent or mixture of solvents such as water, methylene chloride, chloroform, ether, tetrahydrofuran, dioxane or dimethylformamide or in an excess of the acylating agent as solvent with a corresponding carboxylic acid in the presence of an acid activating or dehydrating agent such as thionylchloride, with the anhydrides thereof such as acetic acid anhydride, with the esters thereof such as ethyl acetate, with the halides thereof such as acetyl chloride or methanesulphonyl chloride, optionally in the presence of an inorganic or tertiary organic base, such as sodium hydroxide, potassium carbonate, triethylamine or pyridine, whilst the latter two may simultaneously also be used as solvent, at temperatures between −25° and 100° C., but preferably at temperatures between −10° and 80° C.

In the reactions described hereinbefore, any reactive groups present such as hydroxy, amino or alkylamino groups may be protected during the reaction by conventional protecting groups which are split off again after the reaction.

Examples of protecting groups for a hydroxy group are trimethylsilyl, acetyl, benzoyl, methyl, ethyl, tert.butyl, benzyl or tetrahydropyranyl groups and protecting groups for an amino, alkylamino or imino group are acetyl, benzoyl, ethoxycarbonyl or benzyl groups.

The optional subsequent cleaving of a protecting group used is preferably carried out by hydrolysis in an aqueous solvent, e.g. in water, isopropanol/water, tetrahydrofuran/water or dioxane/water, in the presence of an acid such as hydrochloric acid or sulphuric acid or in the presence of an alkali metal base such as sodium hydroxide or potassium hydroxide, at temperatures between 0° and 100° C., preferably at the boiling temperature of the reaction mixture. However, a benzyl group is preferably split off by hydrogenolysis, e.g. with hydrogen in the presence of a catalyst such as palladium/charcoal in a solvent such as methanol, ethanol, ethyl acetate or glacial acetic acid, optionally with the addition of an acid such as hydrochloric acid at temperatures between 0° and 50° C., but preferably at ambient temperature, under a hydrogen pressure of 1 to 7 bar, preferably 3 to 5 bar.

An isomer mixture of a compound of general formula I thus obtained may, if desired, be separated, preferably by chromatography using a carrier such as silica gel or aluminium oxide.

Moreover, the compounds of general formula I obtained may be converted into the acid addition salts thereof, more particularly for pharmaceutical use into the physiologically acceptable salts thereof with inorganic or organic acids. Suitable acids for this purpose include, for example, hydrochloric acid, hydrobromic acid, sulphuric acid, phosphoric acid, fumaric acid, succinic acid, lactic acid, citric acid, tartaric acid or maleic acid.

Furthermore, the new compounds of general formula I thus obtained, if they contain a carboxy or 1H-tetrazolyl group, may if desired subsequently be converted into the salts thereof with inorganic or organic bases, more particularly for pharmaceutical use into the physiologically acceptable salts thereof. Suitable bases include for example sodium hydroxide, potassium hydroxide, cyclohexylamine, ethanolamine, diethanolamine and triethanolamine.

The compounds of general formulae II to IX used as starting materials are known from the literature in some cases or may be obtained by methods known from the literature.

A compound of general formula II is obtained, for example, by acylation of a corresponding o-amino-nitro compound, followed by reduction of the nitro group and subsequent cyclisation.

The compounds of general formulae IV, V, VI and VII used as starting materials are obtained by cyclising a corresponding o-phenylenediamine or by reduction of a corresponding o-amino-nitro compound, with subsequent reduction of the nitro group, cyclisation of an o-diaminophenyl compound thus obtained and by NH-alkylation of a corresponding 1H-benzimidazole thus obtained, whilst the isomer mixture thus obtained can subsequently be resolved by conventional methods, e.g. by chromatography.

The new compounds of general formula I and the physiologically acceptable salts thereof have valuable pharmacological properties. They are angiotensin-antagonists, particularly angiotensin-II-antagonists.

For example, the compounds:

A=1-hydroxycarbonylmethyl-2-phenyl-5-[(2-ethyl -4,6-dimethyl-imidazo[4,5-b]pyridin-1-yl)-methyl]-benzimidazole-trihydrate, B=1-hydroxycarbonylmethyl-2-phenyl-6-[(2-n-propyl -4-methyl-6-(1-methyl-benzimidazol-2-yl)-benzimidazol-1-yl)-methyl]-benzimidazole and C=1-[(1H-tetrazol-5-yl)-methyl]-2-phenyl-5 -[(2-n-propyl-4-methyl-6-(1-methyl-benzimidazol-2-yl)-benzimidazol-1-yl)-methyl]-benzimidazole were tested for their biological effects as follows:

Description of method: Angiotensin II-receptor bonding

The tissue (rats lung) is homogenised in Tris-buffer (50 mMol Tris, 150 mMol NaCl, 5 mMol EDTA, pH 7.40) and centrifuged twice for 20 minutes at 20,000×g. The finished pellets are resuspended in incubating buffer (50 mMol Tris, 5 mMol $MgCl_2$, 0.2% BSA, pH 7.40) 1:75, based on the moist weight of the tissue. Each 0.1 ml of homogenate is incubated for 60 minutes at 37° C. with 50 pM [$^{125}$I]-angiotensin II (NEN, Dreieich, FRG) with increasing concentrations of the test substance in a total volume of 0.25 ml. Incubation is ended by rapid filtration through glass fiber filter mats. The filters are each washed with 4 ml of ice cold buffer (25 mMol Tris, 2.5 mMol $MgCl_2$, 0.1% BSA, pH 7.40). The bound radioactivity is measured using a gamma-counter. The corresponding $IC_{50}$ value is obtained from the dose-activity curve.

In the test described, substances A to C show the following $IC_{50}$ values:

| Substance | $IC_{50}$ [nM] |
|---|---|
| A | 120 |
| B | 23 |
| C | 2.3 |

Moreover, when the above-mentioned compounds were administered to rats in a dose of 30 mg/kg i.v. no toxic side effects, e.g. no negative inotropic effects and no disorders in heart rhythm, were observed. The compounds are therefore well tolerated.

In view of their pharmacological properties, the new compounds and the physiologically acceptable salts thereof are suitable for the treatment of hypertension and cardiac insufficiency and also for treating ischaemic peripheral circulatory disorders, myocardial ischaemia (angina), for the prevention of the progression of cardiac insufficiency after myocardial infarction and for treating diabetic nephropathy, glaucoma, gastrointestinal diseases and bladder diseases.

The new compounds and the physiologically acceptable salts thereof are also suitable for treating pulmonary diseases, e.g. lung oedema and chronic bronchitis, for preventing arterial re-stenosis after angioplasty, for preventing thickening of blood vessel walls after vascular operations, and for preventing arteriosclerosis and diabetic angiopathy. In view of the effects of angiotensin on the release of acetylcholine and dopamine in the brain, the new angiotensin-antagonists are also suitable for alleviating central nervous system disorders, e.g. depression, Alzheimer's disease, Parkinson syndrome, bulimia and disorders of cognitive function.

The dosage required to achieve these effects in adults is appropriately, when administered intravenously, 20 to 100 mg, preferably 30 to 70 mg, and, when administered orally, 50 to 200 mg, preferably 75 to 150 mg, 1 to 3 times a day. For this purpose, the compounds of general formula I prepared according to the invention, optionally in conjunction with other active substances, such as hypotensives, diuretics and/or calcium antagonists, may be incorporated together with one or more inert conventional carriers and/or diluents, e.g. with corn starch, lactose, glucose, microcrystalline cellulose, magnesium stearate, polyvinylpyrrolidone, citric acid, tartaric acid, water, water/ethanol, water/glycerol, water/sorbitol, water/polyethyleneglycol, propyleneglycol, cetylstearyl alcohol, carboxymethylcellulose or fatty substances such as hard fat or suitable mixtures thereof, in conventional galenic preparations such as plain or coated tablets, capsules, powders, suspensions or suppositories.

Additional active substances which may be included in the combinations mentioned above might be, for example, bendroflumethiazide, chlorothiazide, hydrochlorothiazide, spironolactone, benzothiazide, cyclothiazide, ethacrinic acid, furosemide, metoprolol, prazosine, atenolol, propranolol, (di)hydralazine-hydrochloride, diltiazem, felodipin, nicardipin, nifedipin, nisoldipin and nitrendipin. The dosage for these active substances is appropriately ⅕ of the lowest recommended dose up to ¹⁄₁ of the normally recommended dose, i.e., for example, 15 to 200 mg of hydrochlorothiazide, 125 to 2000 mg of chlorothiazide, 15 to 200 mg of ethacrinic acid, 5 to 80 mg of furosemide, 20 to 480 mg of propranolol, 5 to 60 mg of felodipine, 5 to 60 mg of nifedipin or 5 to 60 mg of nitrendipin.

The Examples which follow are intended to illustrate the invention:

EXAMPLE 1

Mixture of 1-hydroxycarbonylmethyl-2-phenyl-5-[(2 -n-butyl-benzimidazol-1-yl)-methyl]-benzimidazole and 1-hydroxycarbonylmethyl-2-phenyl-6-[(2 -n-butyl-benzimidazol-1-yl)-methyl]-benzimidazole a)
1-(4-Amino-3-nitro-benzyl)-2-n-butyl-benzimidazole 34.5 g (109 mMol) of 1-(4-chloro-3-nitro-benzyl)-2 -n-butyl-benzimidazole are mixed with 200 ml of liquid ammonia and heated to 120° C. for 8 hours in an autoclave. After evaporation of the excess ammonia the crude product thus obtained is recrystallised from about 250 ml of methanol.

Yield: 31.2 g (96% of theory), $R_f$ value: 0.44 (silica gel; methylene chloride/methanol= 19:1)

b) 1-(4-benzoylamino-3-nitro-benzyl)-2-n-butyl -benzimidazole-hydrochloride

A solution of 28.0 g (86 mMol) of 1-(4-amino-3 -nitro-benzyl)-2-n-butyl-benzimidazole and 16.9 g (120 mMol) of benzoylchloride in 500 ml of chlorobenzene is refluxed for 16 hours, then the chlorobenzene is distilled off and the crude product thus obtained is recrystallised from about 300 ml of ethanol/diethylether (2:1).

Yield: 26.0 g (71% of theory), $R_f$ value: 0.59 (silica gel; methylene chloride/methanol= 19:1)

$C_{25}H_{24}N_4O_3 \times HCl$ (428.49)

Calculated: C 64.58 H 5.42 N 12.05

Found: 64.34 5.33 12.17 c) 1-(4-Benzoylamino-3-amino-benzyl)-2-n-butyl-benzimidazole 9.0 g (19.4 mMol) of 1-(4-benzoylamino-3-nitro-benzyl)-2-n-butyl-benzimidazole-hydrochloride, dissolved in 500 ml of methanol, are combined with 1 g of 10% palladium/charcoal and hydrogenated at ambient temperature with 5 bars of hydrogen pressure. After the reaction is complete, the catalyst is filtered off and the filtrate is evaporated to dryness. The product thus obtained is further reacted without any more purification.

Yield: 7.7 g (99.5% of theory), $R_f$ value: 0.38 (silica gel; methylene chloride/methanol= 19:1)

d) 2-phenyl-5-[(2-n-butyl-benzimidazol-1-yl)-methyl]-benzimidazole

A solution of 7.7 g (19.3 mMol) of 1-(4-benzoylamino-3-aminobenzyl)-2-n-butyl-benzimidazole in 100 ml of glacial acetic acid is heated to 100° C. for 2 hours, then about 95 ml of glacial acetic acid are distilled off, the residue is mixed with about 150 ml of water and made alkaline with concentrated ammonia. The crude product precipitated is suction filtered and purified by column chromatography (500 g silica gel; eluant: methylene chloride/methanol:50:1).

Yield: 5.4 g (73% of theory), $R_f$ value: 0.36 (silica gel; methylene chloride/methanol= 19:1)

$C_{25}H_{24}N_4$ (380.49)

Calculated: C 78.92 H 6.36 N 14.72
Found: 78.68 6.43 14.58 e) Mixture of 1-ethoxycarbonylmethyl-2-phenyl-5-[(2-n-butyl-benzimidazol-1-yl)-methyl]-benzimidazole and 1-ethoxycarbonylmethyl-2-phenyl-6-[(2-n-butyl-benzimidazol-1-yl)-methyl]-benzimidazole A solution of 810 mg (7.2 mMol) of potassium tert.butoxide, 2.7 g (7.1 mMol) of 2-phenyl-5-[(2-n-butyl-benzimidazol-1-yl)-methyl]-benzimidazole and 1.2 g (7.2 mMol) of ethyl bromoacetate in 50 ml of dimethylsulphoxide is stirred for 4 hours at ambient temperature, then mixed with about 300 ml of water and extracted three times with about 40 ml of ethyl acetate. The organic extracts are washed with about 30 ml of water, dried and evaporated down. The crude isomer mixture thus obtained is reacted without any further purification.

Yield: 3.3 g (100% of theory), $R_f$ value: 0.42 (silica gel; methylene chloride/methanol= 19:1)

f) Mixture consisting of 1-hydroxycarbonylmethyl-2-phenyl-5-[(2-n-butyl-benzimidazol-1-yl)-methyl]-benzimidazole and 1-hydroxycarbonylmethyl-2-phenyl-6-[(2-n-butyl-benzimidazol-1-yl)-methyl]-benzimidazole 3.3 g (7.0 mMol) of the mixture obtained according to Example 1e are stirred for 4 hours in a solution of 1.2 g (30 mMol) of sodium hydroxide in 20 ml of water and 50 ml of ethanol at ambient temperature. Then the ethanol is distilled off, the residue is diluted with about 30 ml of water, acidified with acetic acid and the crude product precipitated is suction filtered. It is purified by column chromatography (300 g silica gel; eluant=methylene chloride/methanol=9:1).

Yield: 2.0 g (65% of theory),

Melting point: amorphous $R_f$ value: 0.24 (silica gel; methylene chloride/methanol= 9:1)

$C_{27}H_{26}N_4O_2$ (438.53)

Calculated: C 73.95 H 5.98 N 12.78
Found: 73.74 6.05 12.67

EXAMPLE 2

1-Hydroxycarbonylmethyl-2-phenyl-5-[(2-ethyl-5,7-dimethyl-imidazo[4,5-b]pyridin-3-yl)-methyl]-benzimidazole-trihydrate Prepared analogously to Example 1 from 1-ethoxycarbonylmethyl-2-phenyl-5-[(2-ethyl-5,7-dimethylimidazo-[4,5-b]pyridin-3-yl)-methyl]-benzimidazole and aqueous sodium hydroxide solution in ethanol.

Yield: 48% of theory,

Melting point: 170°–172° C.

$R_f$ value: 0.29 (silica gel; methylene chloride/methanol= 8:2)

$C_{26}H_{25}N_5O_2 \times 3H_2O$ (439.52)

Calculated: C 63.27 H 6.33 N 14.19
Found: 63.47 6.12 14.28

EXAMPLE 3

1-Hydroxycarbonylmethyl-2-phenyl-6-[(2-ethyl-5,7-dimethyl-imidazo[4,5-b]pyridin-3-yl)-methyl]-benzimidazole-semihydrate Prepared analogously to Example 1 from 1-ethoxycarbonylmethyl-2-phenyl-5-[(2-ethyl-5,7-dimethyl-imidazo[4,5-b]pyridin-3-yl)-methyl]-benzimidazole and aqueous sodium hydroxide solution in ethanol.

Yield: 57% of theory,

Melting point: 256°–257° C.

$R_f$ value: 0.30 (silica gel; methylene chloride/methanol= 8:2)

$C_{26}H_{25}N_5O_2 \times \frac{1}{2} H_2O$ (439.52)

Calculated: C 69.62 H 5.84 15.61
Found: 69.50 5.91 15.77

EXAMPLE 4

Mixture of the sodium salt of 1-hydroxycarbonylmethyl-2-cyclopropyl-5-[(2-n-propyl-4-methyl-benzimidazol-1-yl)-methyl]-benzimidazole×sodium acetate×2 H_2O and the sodium salt of 1-hydroxycarbonylmethyl-2-cyclopropyl-6-[(2-n-propyl-4-methyl-benzimidazol-1-yl)-methyl]-benzimidazole×sodium acetate×2 H_2O Prepared analogously to Example 1 from a mixture of 1-ethoxycarbonylmethyl-2-cyclopropyl-5-[(2-n-propyl-4-methyl-benzimidazol-1-yl)-methyl]-benzimidazole and 1-ethoxycarbonylmethyl-2-cyclopropyl-6-[(2-n-propyl-4-methyl-benzimidazol-1-yl)-methyl]-benzimidazole and aqueous sodium hydroxide solution in ethanol.

Yield: 80% of theory,

Melting point: amorphous

R_f value: 0.25 (silica gel; methylene chloride/methanol= 8:2)

$C_{24}H_{25}N_4O_2Na \times CH_3COONa \times 2 H_2O$ (542.55)

Calculated: C 57.55 H 5.95 N 10.33
Found: 57.63 5.95 10.18

EXAMPLE 5

1-Hydroxycarbonylmethyl-2-phenyl-6-[(2-n-propyl-4-methyl-6-(1-methyl-benzimidazol-2-yl)-benzimidazol-1-yl)-methyl]-benzimidazole Prepared analogously to Example 1 from 1-ethoxycarbonylmethyl-2-phenyl-6-[(2-n-propyl-4-methyl-6 -(1-methyl-benzimidazol-2-yl)-benzimidazol-1-yl)-methyl]-benzimidazole and aqueous sodium hydroxide solution in ethanol.

Yield: 10% of theory,

Melting point: from 250° C. (decomp.)

R_f value: 0.14 (silica gel; methylene chloride/methanol= 9:1)

$C_{35}H_{32}N_6O_2$ (568.68)

Calculated: C 73.92 H 5.67 N 14.78
Found: 73.73 5.71 14.86

EXAMPLE 6

1-Hydroxycarbonylmethyl-2-phenyl-5-[(2-n-propyl-4-methyl-6-(1-methyl-benzimidazol-2-yl)-benzimidazol-1-yl)-methyl]-benzimidazole Prepared analogously to Example 1 from 1-ethoxycarbonylmethyl-2-phenyl-5-[(2-n-propyl-4-methyl-6 -(1-methyl-benzimidazol-2-yl)-benzimidazol-1-yl)-methyl]-benzimidazole and aqueous sodium hydroxide solution in ethanol.

Yield: 30% of theory,

Melting point: from 235° C. (decomp.)

R_f value: 0.34 (silica gel; methylene chloride/methanol= 9:1)

$C_{35}H_{32}N_6O_2$ (568.68)

Calculated: C 73.92 H 5.67 N 14.78
Found: 73.75 5.71 14.59

EXAMPLE 7

1-[ (1H-Tetrazol-5-yl) -methyl ]-2-phenyl-5-[(2-n-butyl-benzimidazol-1-yl)-methyl]-benzimidazole a) Mixture of 1-cyanomethyl-2-phenyl-5-[(2-n-butyl-benzimidazol-1-yl)-methyl]-benzimidazole and 1-cyanomethyl-2-phenyl-6-[(2-n-butyl-benzimidazol-1-yl)-methyl]-benzimidazole A solution of 2.1 g (5.5 mMol) of 2-phenyl-5-[(2-n-butyl-benzimidazol-1-yl)-methyl]-benzimidazole and 530 mg of chloroacetonitrile in 30 ml of dimethylsulphoxide is mixed with 1.9 g (11 mMol) of potassium carbonate-dihydrate and stirred for 2 hours at 60° C. After cooling, about 100 ml of water are added, then the crude product precipitated is suction filtered and purified by column chromatography (300 g silica gel; eluant: methylene chloride/methanol= 30:1).

Yield: 1.2 g (52% of theory),

R_f value: 0.68 (silica gel; methylene chloride/methanol= 19:1)

b) 1-[(1H-Tetrazol-5-yl)-methyl]-2-phenyl-5-[(2-n-butyl-benzimidazol-1-yl)-methyl]-benzimidazole 1.2 g (2.9 mMol) of the mixture obtained according to Example 7a are dissolved in 25 ml of dimethylformamide, mixed with 3.1 g (57.2 mMol) of ammonium chloride and 3.7 g (57.2 mMol) of sodium azide and stirred for 3 hours at 140° C. Then about 80 ml of water are added and after 2 hours' stirring at ambient temperature the crude product precipitated is suction filtered and dried. In this way, 1.2 g of the isomer mixture of the analogous tetrazole compounds are obtained. By fractional crystallisation from methanol the 5-isomer is obtained therefrom in pure form whilst the 6-isomer is left behind in the mother liquor in concentrated form.

Yield: 0.54 g (41% of theory),

Melting point: sintering from 195° C.

R_f value: 0.40 (silica gel; methylene chloride/methanol= 8:2)

$C_{27}H_{26}N_8$ (462.57)

Calculated: C 70.11 H 5.67 N 24.23
Found: 69.93 5.77 24.10

EXAMPLE 8

1-[(1H-Tetrazol-5-yl)-methyl]-2-phenyl-6-[(2-n-butyl-benzimidazol-1-yl)-methyl]-benzimidazole Prepared by concentrating the mother liquor obtained according to Example 7b and subsequent crystallisation from methanol.

Yield: 0.40 g (30% of theory) ,

Melting point: from 140° C. (decomp.)

R_f value: 0.33 (silica gel; methylene chloride/methanol= 8:2)

$C_{27}H_{26}N_8$ (462.57)

Calculated: C 70.11 H 5.67 N 24.23
Found: 69.96 5.89 24.05

EXAMPLE 9

Mixture of
1-[(1H-tetrazol-5-yl)-methyl]-2-cyclopropyl-5-[(2-n-propyl-4-methyl-benzimidazol-1-yl)-methyl]-benzimidazole and
1-[(1H-tetrazol-5-yl)-methyl]-2-cyclopropyl-6-[(2-n-propyl-4-methyl-benzimidazol-1-yl)-methyl]-benzimidazole Prepared analogously to Example 7b from 1-cyanomethyl-2-cyclopropyl-5-[(2-n-propyl-4-methyl-benzimidazol-1-yl)-methyl]-benzimidazole and 1-cyanomethyl-2-cyclopropyl-6-[(2-n-propyl-4-methyl-benzimidazol-1-yl)-methyl]-benzimidazole and sodium azide in dimethylformamide.

Yield: 52% of theory,

Melting point: 203°–205° C.

R_f value: 0.50 (silica gel; methylene chloride/methanol= 8:2)

$C_{24}H_{26}N_8$ (426.53)

Calculated: C 67.58 H 6.14 N 26.27

Found: 67.47 6.40 26.45

EXAMPLE 10

Mixture of 1-[(1H-tetrazol-5-yl)-methyl]-2-phenyl-5-[(2-ethyl-5,7-dimethyl-imidazo[4,5-b]pyridin-3-yl)-methyl]-benzimidazole and 1-[(1H-tetrazol-5-yl)-methyl]-2-phenyl-6-[(2-ethyl-5,7-dimethyl-imidazo[4,5-b]pyridin-3-yl)-methyl]-benzimidazole Prepared analogously to Example 7b from a mixture of 1-cyanomethyl-2-phenyl-5-[(2-ethyl-5,7-dimethylimidazo[4,5-b]pyridin-3-yl)-methyl]-benzimidazole and 1-cyanomethyl-2-phenyl-6-[(2-ethyl-5,7-dimethylimidazo[ 4,5-b]pyridin-3-yl)-methyl]-benzimidazole and sodium azide in dimethylformamide.

Yield: 37% of theory,

Melting point: 172°–174° C.

$R_f$ value: 0.16 (silica gel; methylene chloride/methanol= 9:1)

$C_{26}H_{25}N_9$ (463.56)

Mass spectrum: m/e=463

EXAMPLE 11

1-[(1H-Tetrazol-5-yl)-methyl]-2-phenyl-5-[(2-n-propyl-4-methyl-6-(1-methyl-benzimidazol-2-yl)-benzimidazol-1-yl)-methyl]-benzimidazole Prepared analogously to Example 7b from 1-cyanomethyl-2-phenyl-5-[(2-n-propyl-4-methyl-6-(1-methyl-benzimidazol-2-yl)-benzimidazol-1-yl)-methyl]-benzimidazole and sodium azide in dimethylformamide.

Yield: 11% of theory,

Melting point: from 203° C. (decomp.)

$R_f$ value: 0.34 (silica gel; methylene chloride/methanol= 9:1)

$C_{35}H_{32}N_{10}$ (592.72)

Calculated: C 70.92 H 5.44 N 23.63

Found: 70.76 5.72 23.57

EXAMPLE 12

1-[(1H-Tetrazol-5-yl)-methyl]-2-phenyl-6-[(2-n-propyl-4-methyl-6-(1-methyl-benzimidazol-2-yl)-benzimidazol-1-yl)-methyl]-benzimidazole-trihydrate Prepared analogously to Example 7b from 1-cyanomethyl-2-phenyl-6-[(2-n-propyl-4-methyl-6-(1-methyl-benzimidazol-2-yl)-benzimidazol-1-yl)-methyl]-benzimidazole and sodium azide in dimethylformamide.

Yield: 12% of theory,

Melting point: from 205° C. (decomp.)

$R_f$ value: 0.11 (silica gel; methylene chloride/methanol= 9:1)

$C_{35}H_{32}N_{10} \times 3H_2O$ (592.72)

Calculated: C 65.00 H 5.92 N 21.65

Found: 65.21 5.76 21.68

In the Examples of Pharmaceutical Formulations which follow, any suitable compound of formula I, particularly those compounds wherein $R_b$ represents a carboxy or 1H-tetrazolyl group, may be used as the active substance:

EXAMPLE 1

| Ampoules containing 50 mg of active substance per 5 ml | |
|---|---|
| Active substance | 50 mg |
| $KH_2PO_4$ | 2 mg |
| $Na_2HPO_4 \times 2H_2O$ | 50 mg |
| NaCl | 12 mg |
| Water for injections –a–d | 5 ml |

Preparation

The buffer substances and isotonic substance are dissolved in some of the water. The active substance is added and, once it has been completely dissolved, water is added to make up the required volume.

EXAMPLE II

| Ampoules containing 100 mg of active substance per 5 ml | |
|---|---|
| Active substance | 100 mg |
| Methyl glucamine | 35 mg |
| Glycofurol | 1000 mg |
| Polyethyleneglycol-polypropylene-glycol block polymer | 250 mg |
| water for injections –a–d | 5 ml |

Preparation

Methyl glucamine is dissolved in some of the water and the active substance is dissolved with stirring and heating. After the addition of solvents, water is added to make up the desired volume.

EXAMPLE III

| Tablets containing 50 mg of active substance | |
|---|---|
| Active substance | 50.0 mg |
| Calcium phosphate | 70.0 mg |
| Lactose | 40.0 mg |
| Corn starch | 35.0 mg |
| Polyvinylpyrrolidone | 3.5 mg |
| Magnesium stearate | 1.5 mg |
| | 200.0 mg |

Preparation

The active substance, $CaHPO_4$, lactose and corn starch are uniformly moistened with an aqueous PVP solution. The mass is passed through a 2 mm screen, dried at 50° C. in a circulating air dryer and screened again.

After the lubricant has been added, the granules are compressed in a tablet making machine.

EXAMPLE IV

| Coated tablets containing 50 mg of active substance | |
|---|---|
| Active substance | 50.0 mg |
| Lysine | 25.0 mg |
| Lactose | 60.0 mg |
| Corn starch | 34.0 mg |
| Gelatin | 10.0 mg |

| Coated tablets containing 50 mg of active substance | |
|---|---|
| Magnesium stearate | 1.0 mg |
| | 180.0 mg |

Preparation

The active substance is mixed with the excipients and moistened with an aqueous gelatin solution. After screening and drying the granules are mixed with magnesium stearate and compressed to form tablet cores.

The cores thus produced are covered with a coating by known methods. A colouring may be added to the coating suspension or solution.

EXAMPLE V

| Coated tablets containing 100 mg of active substance | |
|---|---|
| Active substance | 100.0 mg |
| Lysine | 50.0 mg |
| Lactose | 86.0 mg |
| Corn starch | 50.0 mg |
| Polyvinylpyrrolidone | 2.8 mg |
| Microcrystalline cellulose | 60.0 mg |
| Magnesium stearate | 1.2 mg |
| | 350.0 mg |

Preparation

The active substance is mixed with the excipients and moistened with an aqueous PVP solution. The moist mass is passed through a 1.5 mm screen and dried at 45° C. After drying, it is screened again and the magnesium stearate is added. This mixture is compressed into cores.

The cores thus produced are covered with a coating by known methods. Colourings may be added to the coating suspension or solution.

EXAMPLE VI

| Capsules containing 250 mg of active substance | |
|---|---|
| Active substance | 250.0 mg |
| Corn starch | 68.5 mg |
| Magnesium stearate | 1.5 mg |
| | 320.0 mg |

Preparation

The active substance and corn starch are mixed together and moistened with water. The moist mass is screened and dried. The dry granules are screened and mixed with magnesium stearate. The final mixture is packed into size 1 hard gelatin capsules.

EXAMPLE VII

| Oral suspension containing 50 mg of active substance per 5 ml | |
|---|---|
| Active substance | 50.0 mg |
| Hydroxyethylcellulose | 50.0 mg |

| Oral suspension containing 50 mg of active substance per 5 ml | |
|---|---|
| Sorbic acid | 5.0 mg |
| 70% sorbitol | 600.0 mg |
| Glycerol | 200.0 mg |
| Flavouring | 15.0 mg |
| Water –a–d | 5.0 ml |

Preparation

Distilled water is heated to 70° C. Hydroxyethylcellulose is dissolved therein with stirring. With the addition of sorbitol solution and glycerol the mixture is cooled to ambient temperature. At ambient temperature, sorbic acid, flavouring and active substance are added. The suspension is evacuated with stirring to remove any air. One dose of 50 mg is contained in 5.0 ml.

EXAMPLE VIII

| Suppositories containing 100 mg of active substance | |
|---|---|
| Active substance | 100.0 mg |
| Solid fat | 1600.0 mg |
| | 1700.0 mg |

Preparation

The hard fat is melted. At 40° C. the ground active substance is homogeneously dispersed in the melt. It is cooled to 38° C. and poured into slightly chilled suppository moulds.

What is claimed is:

1. A substituted benzimidazolyl derivative of the formula $$\text{(I)}$$

wherein

A denotes a 1,4-butadienylene group substituted by the groups $R_1$ and $R_2$ and wherein additionally an unsubstituted methine group may be replaced by a nitrogen atom, wherein $R_1$ denotes a hydrogen, fluorine, chlorine or bromine atom, a trifluoromethyl group or a $C_{1-3}$-alkyl group and $R_2$ denotes a hydrogen atom, a $C_{1-3}$-alkyl group, a carboxy group, an alkoxycarbonyl group having a total of 2 to 6 carbon atoms, a $C_{2-5}$-alkoxy group which is substituted in the 2-, 3-, 4- or 5-position by an imidazolyl, benzimidazolyl or tetrahydrobenzimidazolyl group, an alkanoylamino group having 2 to 5 carbon atoms in the alkanoyl moiety or a benzenesulphonylamino group, both of which may be substituted at the nitrogen atom by a $C_{1-3}$-alkyl group, a phthalimino or homophthalimino group, in which a carbonyl group in a phthalimino group may be replaced by a methylene group, a 5-, 6- or 7-membered alkyleneimino group in which a methylene group may be replaced by a carbonyl or sulphonyl group, a glutaric acid imino group in which the n-propylene group may be substituted by one or two $C_{1-3}$-alkyl groups or by a tetramethylene or pentamethylene group, a maleic acid imido group optionally mono- or disubstituted by a $C_{1-3}$-alkyl group or by a phenyl group, in which the substituents may be identical or different, a benzimidazol-2-yl group optionally substituted in the 1-position by a $C_{1-6}$-alkyl group or a $C_{3-7}$-cycloalkyl group, wherein the phenyl nucleus in a benzimidazol-2-yl group mentioned above may additionally be substituted by a fluorine atom or by a methyl or trifluoromethyl group, an imidazo[2,1-b]thiazol-6-yl, imidazo[1,2-a]pyridin-2-yl, 5,6,7,8-tetrahydro-imidazo[1,2-a]pyridin-2-yl, imidazo[1,2-a]pyrimidin-2-yl, imidazo[4,5-b]pyridin-2-yl, imidazo[4,5-c]pyridin-2-yl, imidazo[1,2-c]pyrimidin-2-yl, imidazo[1,2-a]pyrazin-2-yl, imidazo[1,2-b]-pyridazin-2-yl, imidazo[4,5-c]pyridin-2-yl, purin-8-yl, imidazo[4,5-b]pyrazin-2-yl, imidazo[4,5-c]pyridazin-2-yl or imidazo[4,5-d]pyridazin-2-yl group, a pyrrolidine, piperidine or pyridine ring bound via a carbon atom, wherein a phenyl group may be fused onto the pyridine ring via two adjacent carbon atoms and a methylene group adjacent to the N-atom in a pyrrolidine or piperidine ring may be replaced by a carbonyl or sulphonyl group, an imidazol-4-yl group optionally substituted in the 2-position by a $C_{1-6}$-alkyl group or by a phenyl group, and substituted in the 1-position by a $C_{1-7}$-alkyl group (which may be substituted in the 2-, 3-, 4-, 5-, 6- or 7-position by a carboxy, alkoxycarbonyl, aminocarbonyl, alkylaminocarbonyl, dialkylaminocarbonyl, morpholinocarbonyl, thiomorpholinocarbonyl or 1-oxidothiomorpholinocarbonyl group), by a $C_{2-4}$-alkyl group (substituted in the 2-, 3- or 4-position by a hydroxy, alkoxy or imidazol-1-yl group), by an alkyl group (substituted by a trifluoromethyl group, by a $C_{3-7}$-cycloalkyl group or by a phenyl group optionally mono- or disubstituted by fluorine or chlorine atoms or by trifluoromethyl, methyl or methoxy groups), by an alkyl group substituted by two phenyl groups, or by a $C_{3-7}$-cycloalkyl group, whilst unless otherwise specified the above-mentioned alkyl and alkoxy moieties may each contain 1 to 3 carbon atoms, a carboxy, aminocarbonyl, alkylaminocarbonyl or dialkylamino group in which each alkyl moiety may contain 1 to 6 carbon atoms, or a group which is metabolically converted in vivo into a carboxy group, or an $R_5$-$NR_4$-CO-$NR_3$- group wherein $R_3$ denotes a hydrogen atom, a $C_{1-5}$-alkyl group, a cyclohexyl or benzyl group, $R_4$ denotes a hydrogen atom, a $C_{1-6}$-alkyl group, an allyl, cyclohexyl, benzyl or phenyl group, $R_5$ denotes a hydrogen atom or a $C_{1-3}$-alkyl group or $R_4$ and $R_5$ together with the nitrogen atom between them denote an unbranched $C_{4-6}$-cycloalkyleneimino group or a morpholino group or $R_3$ and $R_4$ together denote a $C_{2-3}$-alkylene group, $R_a$ denotes a $C_{1-5}$-alkyl group, a $C_{3-5}$-cycloalkyl group, an alkoxy, alkylthio or alkylamino group each having 1 to 3 carbon atoms in each alkyl moiety, $R_b$ denotes a carboxy, cyano, hydroxysulphonyl, 1H-tetrazolyl, 1-triphenylmethyl-tetrazolyl or 2-triphenylmethyl-tetrazolyl group, a group which is metabolically converted in vivo into a carboxy group, an alkanecarbonylaminosulphonyl, benzoylaminosulphonyl, alkanesulphonylaminocarbonyl, trifluoromethanesulphonylaminocarbonyl or phenylsulphonylaminocarbonyl group, whilst in the above-mentioned groups the alkyl and alkoxy moieties may each contain 1 to 4 carbon atoms, and $R_c$ denotes an alkyl group, a $C_{3-6}$-cycloalkyl group or a phenyl group which may be mono- or disubstituted by a fluorine, chlorine or bromine atom or by a hydroxy, alkoxy or alkyl group, wherein the substituents may be identical or different and the alkyl and alkoxy moieties mentioned in the above-mentioned groups may each contain 1 to 6 carbon atoms, or a pharmaceutically acceptable salt thereof.

2. A substituted benzimidazolyl derivative of the formula I according to claim 1, wherein A, $R_a$ and $R_c$ are defined as in claim 1 and $R_b$ denotes a carboxy or 1H-tetrazolyl group or a group which is metabolically converted in vivo into a carboxy group, said group being of the formulae

-CO-OR',

-CO-O-(HCR")-O-CO-R''' and

-CO-O-(HCR")-O-CO-OR''' wherein

R' denotes a straight-chained or branched $C_{1-6}$-alkyl group, a $C_{5-7}$-cycloalkyl, benzyl, 1-phenylethyl, 2-phenylethyl, 3-phenylpropyl, methoxymethyl or cinnamyl group, R" denotes a hydrogen atom or a methyl group and R''' denotes a straight-chained or branched $C_{1-6}$-alkyl group, a $C_{5-7}$-cycloalkyl, phenyl, benzyl, 1-phenylethyl, 2-phenylethyl or 3-phenylpropyl group, or a pharmaceutically acceptable salt thereof.

3. A substituted benzimidazolyl derivative of the formula I according to claim 1, wherein A denotes a 1,4-butadienylene group substituted by the groups $R_1$ and $R_2$ and wherein additionally the methine group in position 7 of the benzimidazole thus formed may be replaced by a nitrogen atom, wherein $R_1$ denotes a hydrogen atom or in the 4-position a fluorine, chlorine or bromine atom, a trifluoromethyl group or a $C_{1-3}$-alkyl group and $R_2$ denotes a hydrogen atom, a $C_{1-3}$-alkyl group, in the 6-position an alkanoylamino group having 2 to 5 carbon atoms in the alkanoyl moiety or a benzenesulphonylamino group, both of which may be substituted at the nitrogen atom by a $C_{1-3}$-alkyl group, in the 6-position a phthalimino or homophthalimino group, in which a carbonyl group in a phthalimino group may be replaced by a methylene group, in the 6-position a 5-, 6- or 7-membered alkyleneimino group in which a methylene group is replaced by a carbonyl or sulphonyl group, in the 6-position a maleic acid imido group optionally mono- or disubstituted by a $C_{1-3}$-alkyl group or by a phenyl group, wherein the substituents may be identical or different, in the 6-position a benzimidazol-2-yl group optionally substituted in the 1-position by a $C_{1-6}$-alkyl group or by a $C_{3-7}$-cycloalkyl group, wherein the phenyl nucleus in a benzimidazol-2-yl group as mentioned above may additionally be substituted by a fluorine atom or by a methyl or trifluoromethyl group, an imidazo[2,1-b]thiazol-6-yl, imidazo[1,2-a]pyridin-2-yl, 5,6,7,8-tetrahydroimidazo[1,2-a]pyridin-2-yl, imidazo-[1,2-a]pyrimidin-2-yl or imidazo[4,5-b]pyridine2-yl group, in the 6-position an imidazol-4-yl group which may be substituted in the 1-position by a $C_{1-7}$-alkyl group (which may be substituted in the 2-, 3-, 4-, 5-, 6- or 7-position by a carboxy, alkoxycarbonyl, aminocarbonyl, alkylaminocarbonyl, dialkylaminocarbonyl, morpholinocarbonyl, thiomorpholinocarbonyl or 1-oxidothiomorpholinocarbonyl group), by a $C_{2-4}$-alkyl group (substituted in the 2-, 3- or 4-position by a hydroxy, alkoxy or imidazol-1-yl group), by an alkyl group (which is substituted by a trifluoromethyl group, by a $C_{3-7}$-cycloalkyl group or by a phenyl group optionally mono- or disubstituted by fluorine or chlorine atoms or by trifluoromethyl, methyl or methoxy groups), by an alkyl group substituted by two phenyl groups, or by a $C_{3-7}$-cycloalkyl group, whilst unless otherwise specified the above-mentioned alkyl and alkoxy moieties may each contain 1 to 3 carbon atoms, in the 7-position a carboxy, aminocarbonyl, alkylaminocarbonyl or dialkylamino group wherein each alkyl moiety may contain 1 to 6 carbon atoms, or a group which is metabolically converted in vivo into a carboxy group, or in the 6-position an $R_5$-$NR_4$-CO-$NR_3$- group wherein $R_3$ denotes a hydrogen atom, a $C_{1-5}$-alkyl group, a cyclohexyl or benzyl group, $R_4$ denotes a hydrogen atom, a $C_{1-6}$-alkyl group, an allyl, cyclohexyl, benzyl or phenyl group, $R_5$ denotes a hydrogen atom or a $C_{1-3}$-alkyl group or $R_4$ and $R_5$ together with the nitrogen atom between them denote an unbranched $C_{4-6}$-cycloalkyleneimino group or a morpholino group or $R_3$ and $R_4$ together denote a $C_{2-3}$-alkylene group, $R_a$ denotes a $C_{2-4}$-alkyl group, a $C_{3-4}$-cycloalkyl group or a $C_{2-3}$-alkoxy group, $R_b$ denotes a carboxy or 1 H-tetrazolyl group or a group which is metabolically converted in vivo into a carboxy group, said group being of the formulae

-CO-OR',

-CO-O-(HCR'')-O-CO-R''' and

-CO-O-(HCR'')-O-CO-OR''' wherein

R' denotes a straight-chained or branched $C_{1-6}$-alkyl group, a $C_{5-7}$-cycloalkyl, benzyl, 1-phenylethyl, 2-phenylethyl, 3-phenylpropyl, methoxymethyl or cinnamyl group, R'' denotes a hydrogen atom or a methyl group and R''' denotes a straight-chained or branched $C_{1-6}$-alkyl group, a $C_{5-7}$-cycloalkyl, phenyl, benzyl, 1-phenylethyl, 2-phenylethyl or 3-phenylpropyl group, and $R_c$ denotes a $C_{1-3}$-alkyl group, a $C_{1-6}$-cycloalkyl group or a phenyl group, or a pharmaceutically acceptable salt thereof.

4. A substituted benzimidazolyl derivative of the formula I according to claim 1, wherein A denotes a 1,4-butadienylene group in which the methine group in positions 4 and 6 of the benzimidazole thus formed are substituted by methyl groups and the methine group in position 7 is replaced by a nitrogen atom, or A denotes a 1,4-butadienylene group which is substituted by the groups $R_1$ and $R_2$, wherein $R_1$ denotes a hydrogen atom or in the 4-position a methyl group and $R_2$ in the 6-position denotes a 1-methyl-benzimidazol-2-yl group, $R_a$ denotes a $C_{2-4}$-n-alkyl group, $R_b$ denotes a carboxy or 1H-tetrazolyl group and $R_c$ denotes a $C_{1-3}$-alkyl group, a $C_{3-6}$-cycloalkyl group or a phenyl group, or a pharmaceutically acceptable salt thereof.

5. A compound selected from the group consisting of:

1-hydroxycarbonylmethyl-2-phenyl-5[(2-ethyl-5,7-dimethylimidazo[4,5b]pyridin-3-yl)-methyl]-benzimidazole, 1-hydroxycarbonylmethyl-2-phenyl-6-[(2-n-propyl-4-methyl-6-(1-methyl-benzimidazol-2-yl)-benzimidazol-1-yl)-methyl]-benzimidazole and 1-[(1H-tetrazol-5-yl)-methyl]-2-phenyl-5-[(2-n-propyl-4-methyl-6-(1-methylbenzimidazol-2-yl)-benzimidazol-1-yl)-methyl]-benzimidazole, and the pharmaceutically acceptable salts thereof.

6. A pharmaceutical composition, suitable for the treatment of hypertension or cardiac insufficiency, containing a thereapeutic amount of a compound according to claim 1, 2, 3, 4, or 5 and a pharmaceutically acceptable diluent.

7. A method for treating hypertension in a mammal which comprises administering to a mammal suffering from hypertension a therapeutic amount of a compound according to claims 1, 2, 3, 4, or 5.

8. A method for treating cardiac insufficiency in a mammal which comprises administering to a mammal suffering from cardiac insufficiency a therapeutic amount of a compound according to claims 1, 2, 3, 4, or 5.

9. A method for treating an ischaemic peripheral circulatory disorder in a mammal which comprises administering to a mammal suffering from the same a therapeutic amount of a compound according to claims 1, 2, 3, 4, or 5.

10. A method for treating myocardial ischaemia in a mammal which comprises administering to a mammal suffering from the same a therapeutic amount of a compound according to claims 1, 2, 3, 4, or 5.

11. A method for treating diabetic nephropathy in a mammal which comprises administering to a mammal suffering from the same a therapeutic amount of a compound according to claims 1, 2, 3, 4, or 5.

12. A method for treating glaucoma in a mammal which comprises administering to a mammal suffering from the same a therapeutic amount of a compound according to claims 1, 2, 3, 4, or 5.

* * * * *